United States Patent
Mosher et al.

(10) Patent No.: US 7,251,531 B2
(45) Date of Patent: Jul. 31, 2007

(54) HEATING METHOD FOR TISSUE CONTRACTION

(75) Inventors: Oren A. Mosher, Castro Valley, CA (US); Abdul M. Tayeb, San Leandro, CA (US)

(73) Assignee: AMS Research Corporation, Minnetonka, MN (US)

( * ) Notice: Subject to any disclaimer, the term of this patent is extended or adjusted under 35 U.S.C. 154(b) by 507 days.

(21) Appl. No.: 10/768,780

(22) Filed: Jan. 30, 2004

(65) Prior Publication Data

US 2005/0171583 A1   Aug. 4, 2005

(51) Int. Cl.
*A61F 7/00*   (2006.01)

(52) U.S. Cl. .......................... 607/102; 607/96; 607/99; 607/101

(58) Field of Classification Search ................. 607/96, 607/98–99, 101–102, 113; 606/34, 40, 41, 606/49
See application file for complete search history.

(56) References Cited

U.S. PATENT DOCUMENTS

| | | |
|---|---|---|
| 728,883 A | 5/1903 | Downes |
| 4,679,561 A | 7/1987 | Doss |
| 4,765,331 A | 8/1988 | Petruzzi et al. |
| 5,057,105 A | 10/1991 | Malone et al. |
| 5,201,732 A | 4/1993 | Parins et al. |
| 5,282,799 A | 2/1994 | Rydell |
| 5,423,811 A | 6/1995 | Imran et al. |
| 5,458,596 A | 10/1995 | Lax et al. |
| 5,496,312 A | 3/1996 | Klicek |
| 5,514,130 A | 5/1996 | Baker |
| RE35,330 E | 9/1996 | Malone et al. |
| 5,556,396 A | 9/1996 | Cohen et al. |
| 5,569,242 A | 10/1996 | Lax et al. |
| 5,683,384 A | 11/1997 | Gough et al. |
| 5,853,409 A | 12/1998 | Swanson et al. |
| 5,935,079 A | 8/1999 | Swanson et al. |
| 5,957,920 A | 9/1999 | Baker |
| 6,035,238 A | 3/2000 | Ingle et al. |
| 6,044,847 A | 4/2000 | Carter et al. |
| 6,063,078 A | 5/2000 | Wittkampf |
| 6,081,749 A | 6/2000 | Ingle et al. |
| 6,091,995 A | 7/2000 | Ingle et al. |
| 6,139,569 A | 10/2000 | Ingle et al. |

(Continued)

OTHER PUBLICATIONS

Fulmer, B.R. et al., *Acute and Long-Term Outcomes of Radio Frequency Bladder Neck Suspension*, J. Urology, 167:141-145, (2002).

(Continued)

*Primary Examiner*—Roy D. Gibson
(74) *Attorney, Agent, or Firm*—Barbara A. Wrigley; Oppenheimer Wolff & Donnelly LLP; José W. Jimenez

(57) ABSTRACT

Systems, software, devices, and methods are disclosed for therapeutically heating a collagenous structural support tissue within a pelvic support system of a patient body. The present invention may monitor the delivery of energy and dynamically adjust the delivery of energy during the treatment so that an actual treatment time for reaching a target temperature falls within a desired treatment time range of reaching the target temperature. The present invention may also dynamically adjust the power level after the target temperature has been reached so that the tissue is held at the target temperature for a desired dwell time.

35 Claims, 11 Drawing Sheets

U.S. PATENT DOCUMENTS

| | | | |
|---|---|---|---|
| 6,149,647 A | 11/2000 | Tu et al. | |
| 6,156,060 A | 12/2000 | Roy et al. | |
| 6,183,468 B1 | 2/2001 | Swanson et al. | |
| 6,197,022 B1 | 3/2001 | Baker | |
| 6,216,704 B1 | 4/2001 | Ingle et al. | |
| 6,217,574 B1 | 4/2001 | Webster | |
| 6,236,891 B1 | 5/2001 | Ingle et al. | |
| 6,264,653 B1 | 7/2001 | Falwell | |
| 6,273,886 B1 | 8/2001 | Edwards et al. | |
| 6,283,987 B1 | 9/2001 | Laird et al. | |
| 6,292,700 B1 | 9/2001 | Morrison et al. | |
| 6,293,941 B1 | 9/2001 | Strul et al. | |
| 6,322,584 B2 | 11/2001 | Ingle et al. | |
| 6,391,024 B1 | 5/2002 | Sun et al. | |
| 6,413,255 B1 | 7/2002 | Stern | |
| 6,416,504 B2 | 7/2002 | Mosel et al. | |
| 6,461,332 B1 | 10/2002 | Mosel et al. | |
| 6,480,746 B1 | 11/2002 | Ingle et al. | |
| 6,533,780 B1 | 3/2003 | Laird et al. | |
| 6,546,934 B1 | 4/2003 | Ingle et al. | |
| 6,572,639 B1 | 6/2003 | Ingle et al. | |
| 6,579,266 B2 | 6/2003 | Mosel et al. | |
| 6,587,731 B1 | 7/2003 | Ingle et al. | |
| 6,685,623 B2 | 2/2004 | Presthus et al. | |
| 6,743,165 B2 | 6/2004 | Mosel et al. | |
| 6,772,013 B1 | 8/2004 | Ingle et al. | |
| 6,776,779 B1 | 8/2004 | Roy et al. | |
| 6,830,052 B2 | 12/2004 | Carter et al. | |
| 6,836,688 B2 | 12/2004 | Ingle et al. | |
| 6,840,954 B2 | 1/2005 | Dietz et al. | |
| 6,852,110 B2 | 2/2005 | Roy et al. | |
| 2001/0014819 A1 | 8/2001 | Ingle et al. | |
| 2001/0018606 A1 | 8/2001 | Ingle et al. | |
| 2002/0049483 A1 | 4/2002 | Knowlton | |
| 2002/0111586 A1 | 8/2002 | Mosel et al. | |
| 2003/0144576 A1 | 7/2003 | Presthus et al. | |
| 2003/0181965 A1 | 9/2003 | Levy et al. | |

OTHER PUBLICATIONS

SURx® Press Release. *SURx® Expands Radio Frequency Product Family with New Transvaginal System for Urinary Incontinence* (Mar. 22, 2002) 2 pages total.

SURx® Press Release, *SURx® Receives FDA Clearance to Market Radio Frequency Bladder Neck Suspension Treatment for Female Urinary Incontinence*(Jan. 29, 2002) 2 pages total.

SURx®, *Recent News* http:://surx.com/index.cfm?SCREEN=surx&page=abNews (©2001) printed from web Aug. 14, 2002, 2 pages total.

U.S. Appl. No. 10/759,732, filed Jan. 15, 2004, Mosher et al.
U.S. Appl. No. 10/768,778, filed Jan. 30, 2004, Matlock.
U.S. Appl. No. 10/768,780, filed Jan. 30, 2004, Mosher et al.
U.S. Appl. No. 60/022,790, filed Jul. 30, 1996, Baker.
U.S. Appl. No. 60/024,974, filed Aug. 30, 1996, Baker.

HEATING METHOD FOR TISSUE CONTRACTION

BACKGROUND OF THE INVENTION

The present invention generally relates to medical devices, methods, software, and systems. More specifically, the present invention provides techniques for selectively heating and shrinking tissues, particularly for the noninvasive treatment of urinary incontinence, hernias, cosmetic surgery, and the like.

Urinary incontinence arises in both women and men with varying degrees of severity, and from different causes. In men, the condition occurs almost exclusively as a result of prostatectomies which result in mechanical damage to the sphincter. In women, the condition typically arises after pregnancy where musculoskeletal damage has occurred as a result of inelastic stretching of the structures which support the genitourinary tract. Specifically, pregnancy can result in inelastic stretching of the pelvic floor, the external sphincter, and most often, to the tissue structures which support the bladder and bladder neck region. In each of these cases, urinary leakage typically occurs when a patient's intra-abdominal pressure increases as a result of stress, e.g. coughing, sneezing, laughing, exercise, or the like.

Treatment of urinary incontinence can take a variety of forms. Most simply, the patient can wear absorptive devices or clothing, which is often sufficient for minor leakage events. Alternatively or additionally, patients may undertake exercises intended to strengthen the muscles in the pelvic region, or may attempt behavior modification intended to reduce the incidence of urinary leakage.

In cases where such non-interventional approaches are inadequate or unacceptable, the patient may undergo surgery to correct the problem. A variety of procedures have been developed to correct urinary incontinence in women. Several of these procedures are specifically intended to support the bladder neck region. For example, sutures, straps, or other artificial structures are often looped around the bladder neck and affixed to the pelvis, the endopelvic fascia, the ligaments which support the bladder, or the like. Other procedures involve surgical injections of bulking agents, inflatable balloons, or other elements to mechanically support the bladder neck.

Each of these procedures has associated shortcomings. Surgical operations which involve suturing of the tissue structures supporting the urethra or bladder neck region require great skill and care to achieve the proper level of artificial support. In other words, it is necessary to occlude or support the tissues sufficiently to inhibit urinary leakage, but not so much that intentional voiding is made difficult or impossible. Balloons and other bulking agents which have been inserted can migrate or be absorbed by the body. The presence of such inserts can also be a source of urinary tract infections. Therefore, it would be desirable to provide an improved therapy for urinary incontinence.

A variety of other problems can arise when the support tissues of the body have excessive length. Excessive length of the pelvic support tissues (particularly the ligaments and fascia of the pelvic area) can lead to a variety of ailments including, for example, cystocele, in which a portion of the bladder protrudes into the vagina. Excessive length of the tissues supporting the breast may cause the breasts to sag. Many hernias are the result of a strained, torn, and/or distended containing tissue, which allows some other tissue or organ to protrude beyond its contained position. Cosmetic surgeries are also often performed to decrease the length of support tissues. For example, abdominoplasty (often called a "tummy tuck") is often performed to decrease the circumference of the abdominal wall. The distortion of these support tissues may be due to strain, advanced age, congenital predisposition, or the like.

Unfortunately, many support tissues are difficult to access, and their tough, fibrous nature can complicate their repair. As a result, the therapies now used to improve or enhance the support provided by the ligaments and fascia of the body often involve quite invasive surgical procedures.

For these reasons, it would be desirable to provide improved devices, methods, and systems for treating fascia, tendons, and the other support tissues of the body. It would be particularly desirable to provide improved noninvasive or minimally invasive therapies for these support tissues, especially for the treatment of urinary incontinence in men and women. It would further be desirable to provide treatment methods which made use of the existing support structures of the body, rather than depending on the specific length of an artificial support structure.

BRIEF SUMMARY OF THE INVENTION

The present invention provides systems, methods, device, and software for controlling the delivery of a therapeutic energy that can heat and strengthen a collagenous support structure tissue within a pelvic support system of a patient body.

The present invention provides methods, systems, and computer implemented algorithms that dynamically adjust power delivery so that a target tissue temperature is reached in substantially a desired time. The present invention also provides methods, systems, and computer implemented algorithms that incorporate a dwell time during heat treatment to increase the amount of support tissue that is held above a target temperature for a desired time.

In one particular aspect, the present invention provides a method of heating a support structure tissue of a pelvic support system. The method may comprise delivering energy to the structural support tissue to heat the support structure tissue. A treatment time of reaching the target temperature may be estimated and compared with desired treatment time(s). A power level of the delivered energy may be adjusted if the estimated treatment time is not coincident with the desired treatment time(s).

The estimated treatment time may be calculated by monitoring the effect of the delivery of energy on the structural support tissue. In particular, estimating the treatment time may comprise measuring an elapsed time of delivery of the energy to the structural support tissue and measuring a temperature of the tissue and a temperature rate of change of the structural support tissue. The elapsed time of delivery of the energy, measured temperature of the target zone, and temperature rate of change at the structural support tissue are then used to calculate the estimated treatment time.

The estimation of the treatment time may be performed at predetermined intervals during the delivery of energy so as to allow for multiple estimated treatment times and multiple power level adjustments during the delivery of energy to the structural support tissue. For example, in one embodiment, the estimation of the treatment time (e.g., measuring the elapsed time, temperature of the structural support tissue, and the temperature rate of change) may be repeated every six seconds and the adjustment of delivery of energy (if needed) may be carried out after each estimation of treatment time.

Preferably, the measurement of the temperature and the temperature rate of change at the structural support tissue is commenced only after a predetermined amount of time after beginning of the delivery of energy. Applicants have found that after the predetermined amount has elapsed that an initial heating spike is finished and a rate of heating is declining. In some embodiments, the predetermined amount of time is between approximately 40 seconds and 45 seconds, and preferably about 42 seconds after the commencement of the heat treatment. As can be appreciated, however, the predetermined amount of time will vary depending on the tissue being treated, the power level of the energy being delivered, the configuration of the electrodes on the applicator, and the like. Consequently, estimating the treatment time may be carried out at any desired time after the commencement of the delivery of energy.

To reduce the effect of rapid instantaneous temperature oscillations or rapid instantaneous temperature changes, for the calculations of the present invention the temperature and temperature rate of change may be a smoothed, running average of the temperature and temperature rate of change over the predetermined interval (e.g., six seconds).

During adjustments of the power level, the power level may be adjusted to any different level, but is typically adjusted ±1 Watts or less, ±2 Watts or less, or ±5 Watts or less from its previous power level. The power may be adjusted by a preset stepwise adjustments or the power may be adjusted to any other power level selected by the software that is run by the controller, if desired. For example, the adjusted power level may be based on the difference between the estimated treatment time and the desired treatment time(s). If there is an overly excessive difference between the estimated treatment time and the desired treatment time, the power adjustment may be large (e.g., ±2 Watts). However, if there is only a small difference between the estimated treatment time and the desired treatment time(s), then the power adjustment may be a smaller amount (e.g., ±½ Watt).

If the estimated treatment time is less than the desired treatment time(s) (e.g., treatment is too fast), then the power level is adjusted to a lower level than the original power level. In contrast, if the estimated treatment time is longer than the desired treatment time(s) (e.g., treatment is too slow), then the power level is adjusted to a higher level than the original power level.

The target treatment temperatures of the present invention should be sufficient to cause tissue strengthening, tightening, and/or contraction of the target tissue. The target temperature may be anywhere between approximately 60° C. and approximately 80° C., and preferably between approximately 65° C. and 75° C., and more preferably between approximately 69° C. and 71° C. The desired treatment time(s) will vary depending on the tissue being treated, power level, whether or not cooling is occurring, and the like. In one embodiment, the desired treatment time is between 175 seconds and 185 seconds. While a range is preferred, it may be possible to have the desired treatment time be an exact time, e.g., 175 seconds.

In another aspect, the present invention provides a system for delivering energy to a collagenous structural support tissue of a pelvic support system. The system includes a memory coupled to a processor. The memory can be configured to store a plurality of code modules for execution by the processor. The plurality of code modules include inter alia a code module for delivering energy to the tissue; a code module for estimating a treatment time of reaching a target temperature; a code module for comparing the estimated treatment time with desired treatment time(s); and a code module for adjusting the delivery of the energy to an adjusted power level if the estimated treatment time is not coincident with the desired treatment time(s).

The module for estimating the treatment time may include a module that measure an elapsed time of delivering energy to the structural support tissue; a module for measuring a temperature and a temperature rate of change; and a module for using the measured elapsed time, measured temperature and temperature rate of change to calculate the estimated treatment time.

The system may include a power supply coupled to the processor, such as a Radiofrequency (RF) power supply. An applicator may be coupled to the power supply for delivering the RF energy to the support structure tissue. Some applicators and system that may be used to deliver the RF energy are described in U.S. patent application Ser. No. 09/229,508, filed Jan. 12, 1999 (issued Sep. 14, 2001 as U.S. Pat. No. 6,283,297), U.S. patent application Ser. No. 60/440,711, filed Jan. 16, 2003, U.S. patent application Ser. No. 10/102,596, filed Mar. 19, 2002 (issued Apr. 19, 2005 as U.S. Pat. No. 6,882,885), and U.S. patent application Ser. No. 10/759,732, filed Jan. 15, 2004 (published Sep. 30, 2004 as U.S. Publication No. 2004/0193238 A1 the full disclosures of which is incorporated herein by reference.

The code module for estimating the treatment time of reaching the target temperature may comprise a code module for measuring an elapsed time of delivering energy to the structural support tissue, a code module for measuring a temperature and a temperature rate of change at the structural support tissue, and a code module for using the measured elapsed time, measured temperature and temperature rate of change to calculate an estimated treatment time.

In a further aspect, the present invention provides a method of therapeutically heating a collagenous structural support tissue of a pelvic support system. The method comprises delivering energy to raise a temperature of the structural support tissue to a target temperature. A power level of the energy is dynamically adjusted after the structural support tissue has substantially reached a first target temperature so as to allow the structural support tissue to dwell at substantially a second target temperature for a desired amount of dwell time.

The first and second target temperature may be the same temperature or different temperatures. The first and second target temperatures are typically between approximately 70° C. and approximately 75° C. The desired dwell time is typically at least 30 seconds, and preferably between approximately 30 seconds and approximately 45 seconds. As can be appreciated, a variety of different dwell time may be used with the methods of the present invention, and the invention is not limited to the specific dwell periods recited herein.

The energy level may be optionally be adjusted one or more times during the dwell time to maintain the tissue at substantially the target temperature. In one embodiment, the temperature may be continuously measured. If the average measured temperature of the support tissue is not within an acceptable range from the target temperature, the power level may be adjusted at selected intervals during the dwell time.

Adjustment of the delivery of energy typically comprises lowering the power level. In other embodiments, however, adjusting the energy may comprise raising the power level. The power level may be raised or lowered to any desired level, but is typically adjusted less than approximately 2 W per adjustment. Moreover, there is typically an overall wattage level limit so as to reduce the possibility of damage to the tissue.

In another aspect of the present invention, a system is disclosed for delivering energy to a structural support tissue of a pelvic support system. The system comprises a memory coupled to a processor. The memory is configured to store a plurality of code modules for execution by the processor. The plurality of code modules comprise a code module for delivering energy to raise a temperature of the structural support tissue to a first target temperature and a code module for dynamically adjusting a power level of the energy after the structural support tissue has substantially reached the first target temperature so as to allow the structural support tissue to dwell at substantially a second target temperature for a desired amount of dwell time. The first and second target temperatures may be the same temperature or a different temperature.

The system may include a power supply that is coupled to the processor, such as a Radiofrequency power supply. An applicator is coupleable to the power supply so as to deliver the energy to the target tissue. The applicator may be sized and configured to laparoscopically or transvaginally access the support structure tissue.

In yet another aspect, the present invention provides a method of treating a tissue of structural support tissue of a pelvic support system. The method comprises delivering energy to the structural support tissue at a first power level. A treatment time of reaching a first target temperature is estimated and the estimated treatment time is compared with desired treatment time(s). The delivery of the energy is adjusted to an adjusted power level if the estimated treatment time is not coincident with the desired treatment time(s) such that the adjusted delivery of energy is sufficient to cause the target first temperature to be reached in substantially the desired treatment time(s). After the structural support tissue has substantially reached the first target temperature, a power level of the energy is dynamically adjusted to a modified power level so as to allow the structural support tissue to dwell at substantially a second target temperature for a desired amount of dwell time. Similar to the other embodiments, the first target temperature and the second target temperature may be the same or different temperature.

The above aspects and other aspects of the present invention may be more fully understood from the following detailed description, taken together with the accompanying drawings.

DETAILED DESCRIPTION OF THE INVENTION

Figure 1:
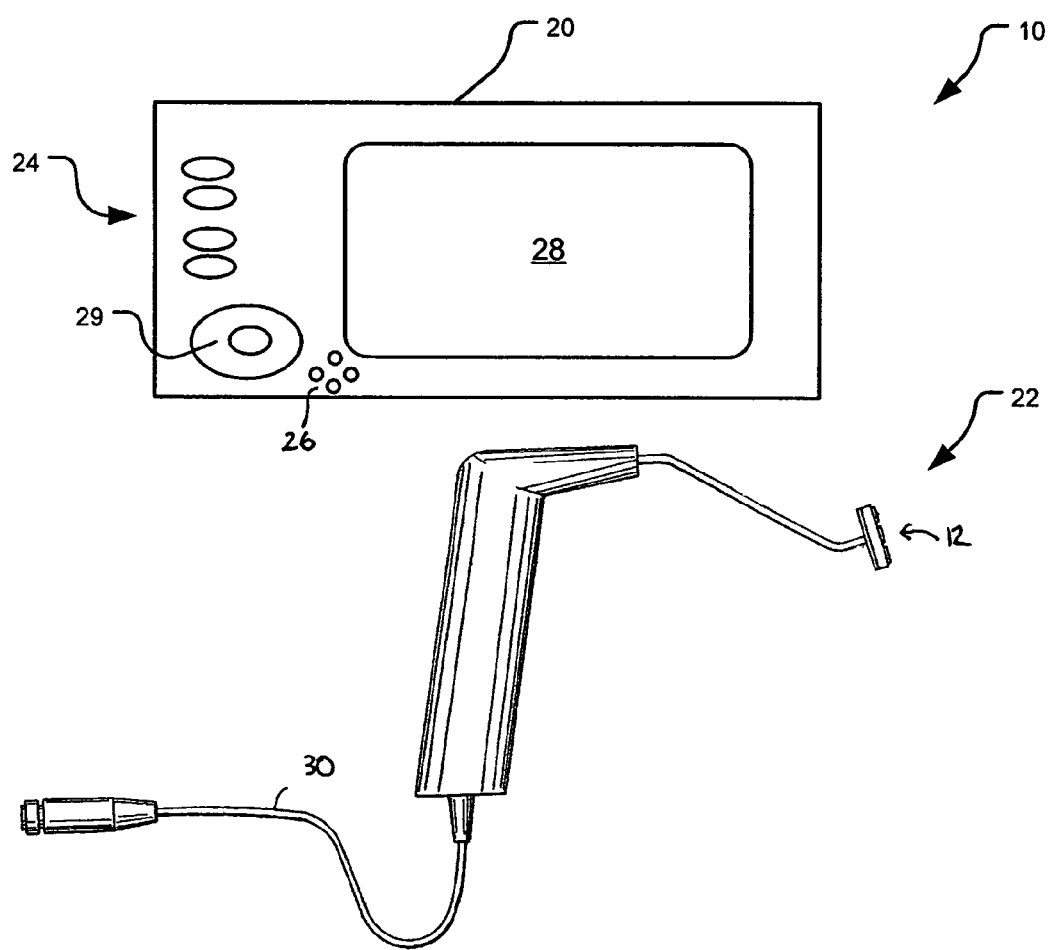
FIG. 1 is a simplified system that includes a control unit and a non-cooled multi-electrode applicator which incorporates the principles of the present invention.

The present invention provides methods, devices, systems, and software algorithms for controlling delivery of energy to body's support tissue to enhance the structural support provided by the body's support tissues. The present invention may be directed to inducing controlled stiffening, contraction, or shrinkage of the structural support tissue of the body, typically being a collagenous tissue such as fascia, ligament, or the like.

For example, in one specific use, the present invention is for treatment of urinary incontinence. The structural support tissue will be part of a pelvic support system that is responsible in some manner for control of urination, or for supporting such a tissue. The tissues of the pelvic support system generally maintain the position of the genitourinary tract, and particularly the position of urinary bladder, urethra, and the bladder neck coupling these structures. In general, endopelvic fascia may define a hammock-like structure which extends laterally between the left and right arcus tendineus fasciae pelvis (ATFP). These tendon structures may extend substantially between the anterior and posterior portions of the pelvis, so that the endopelvic fascia EF at least partially defines the pelvic floor.

The fascial tissue of the pelvic support system may comprise tissues referred to under different names by surgeons of different disciplines, and possibly even by different practitioners within a specialty. In fact, some surgeons may assign a collagenous support structure of the endopelvic fascia one name when viewed from a superior approach, and a different name when viewed from an inferior approach. Some of the endopelvic fascia may comprise two collagenous layers with a thin muscular layer therebetween, or may comprise a single collagenous layer. The hammock-like endopelvic fascia described herein may be damaged or missing, particularly after pregnancy, so that the support of the genitourinary tract is instead provided by a variety of fascial layers, muscular tissues, ligaments, and/or tendons within the pelvis. Hence, the treatment of the present invention may be directed at a variety of tissue structures defining the pelvic floor and/or diaphragm (including: anterior sacrococcygeal ligament; arcus tendineus fasciae pelvis ATFP, the white line of the pelvis; fasciae of the obturator internus muscle; the arcus tendineus levator ani or "picket fence" to the iliococcygeus portion of the levator ani muscle; bulbocavemosus muscle; ischiocavemosus muscle; urethrovaginal sphincter; m. compressor urethrae muscle; and m. sphincter urethrovaginal muscle which replaces deep perineal muscle); structures of the bladder and urethra (including: urethrovesical fascia; detrusor muscle; and the pubo-coccygeus muscle which relaxes to open the bladder neck, initiating micturition); structures of the vagina (including: vagino-uterine fascia, lamina propria—the dense connective tissue layer just under the epithelium; pubourethral or puboprostatic ligaments; pubo-vesicle ligament and posterior pubo-urethral or puboprostatic ligament; pubovesicle muscle, a smooth muscle that is integrated with the pubovesicle ligament; and pubocervical fascia which attaches to the ATFP); structures of the uterus (including: round ligament; sacrouterine ligament; and broad ligament); and structures of the bowel (including: rectal fascia and mackenrodt's ligament).

When the endopelvic fascia has excessive length or stretches excessively under a load, the fluid pressure within the bladder advances into the bladder neck and down the urethra more readily. Leakage may result in part because the endopelvic fascia allows the bladder, bladder neck, and/or urethra to drop below its desired position, at which fluid pressure within the bladder may actually help to seal the bladder neck. Stretching of the endopelvic fascia may also alter the timing of pressure pulse transmission to the urethra.

When a continent woman coughs, the pressure in the urethra will often increase more than one-tenth of a second prior to the increase in bladder pressure. In women with stress incontinence, the bladder pressure may rise first. For a continent woman having endopelvic fascia which stretches much less under the influence of a pressure pulse, the time delay between initiation of the pressure pulse and transferring sufficient force to urethra U to effect closure may therefore be significantly less. By treating the endopelvic fascia to decrease its length and/or increase its stiffness, the descent time of the pelvic viscera during a cough will be shorter than an untreated, excessively long and/or excessively elastic tissue.

The support tissue may be treated non-surgically or it may be accessed for direct treatment in a variety of ways. When using a multi-electrode applicator, for example, the surface of the endopelvic fascia (or other tissue) may be accessed transvaginally by forming and displacing a flap from the vaginal wall with the assistance of a weighted speculum. Alternatively, the endopelvic fascia may be accessed laparoscopically. When using the non-invasive cooled electrode applicator, the tissue may be accessed directly by placing the applicator on the anterior vaginal wall.

Tissue contraction or stiffening results from controlled heating of the tissue by affecting the collagen molecules of the tissue. Contraction occurs as a result of heat-induced uncoiling and repositioning of the collagen β-pleated structure. By maintaining the times and temperatures set forth below, significant tissue contraction can be achieved without substantial collateral tissue necrosis. Stiffening results from the loss of elasticity of the tissue due to the formation of scar tissue and/or attachment of adjacent support tissues to each other as a result of controlled heating of the tissue.

The temperature of the target tissue structure will generally be raised to a value in the range from about 60° C. to 110° C., often being in the range from about 60° C. to 80° C., preferably in the range from about 65° C. to 75° C., and more preferably from about 69° C. to 75° C. Such heating will generally effect a shrinkage of the target tissue in at least one dimension of between about 15 percent and 50 percent, and preferably at least about 40 percent. Alternatively, the temperature of the target tissue structure will generally be raised to value in the range of 45° C. to 60° C. and will generally effect stiffening of the target tissue. The rise in temperature may be quite fast, although there will often be advantages in heating tissues more slowly, as this will allow sufficient heat to be removed from tissues which are not targeted for therapy, thereby minimizing collateral damage. However, if too little heating energy is absorbed by the tissue, blood perfusion will transfer the heat away from the targeted tissue, so that the temperature will not rise sufficiently to effect therapy.

The total amount of energy delivered will depend in part on which tissue structure is being treated, how much tissue is disposed between the target tissue and the heating element, whether or not the electrodes are cooled, and the specific temperature and time selected for the protocol. The power delivered will often be in the range from about 2 W to about 100 W, usually being about 2 W to about 50 W, and preferably between about 12 W and 40 W. For example, in one embodiment using a non-cooled multi-electrode applicator, the power is delivered in a range of about 12 W to about 15 W. During dwell (described below), the power may be varied between 5 W and 7 W. In another example, using the non-invasive, cooled electrode applicator, the power may initially be delivered in a range of about 20 W±5 W for a first time period, and thereafter delivered in a range of about 30 W to about 40 W for a second time period. In a typical case the power is decreased or increased by 1 W to 3 W during the second time period. During dwell (e.g., a third time period), the power may be varied by ±0 W to ±10 W from the original power level. As can be appreciated, the power levels used in the present invention will vary depending on the electrode size, whether or not cooling is used, electrode spacing, as well as the ability of the tissue to accept power. For example, a cooled electrode applicator can deliver a much higher RF power level than a non-cooled electrode applicator since the tissue heating effect is the net of the heating and cooling process.

The temperature of the target zone will usually not drop instantaneously when the heating energy stops, so that the tissue may remain at or near the therapy temperature for a time from about 10 seconds to about 2 minutes, and typically about 15 seconds, and will often cool gradually back to body temperature.

While the remaining description is generally directed to a system for treatment of urinary stress incontinence of a female patient, it will be appreciated that the present invention will find many other applications for selectively directing therapeutic heating energy into the tissues of a patient body. For example, treatment of other conditions may be effected by selective ablation, shrinking or stiffening of a wide variety of other tissues, including (but not limited to) the diaphragm, esophagus, the nasal concha, the abdominal wall, the breast supporting ligaments, the fascia and ligaments of the joints, the collagenous tissues of the skin, tumors, and the like.

FIG. 1 illustrates a simplified system 10 that incorporates the principles of the present invention. System 10 generally includes a control unit 20 that controls a delivery of energy to electrodes 12 on an applicator 22. Control unit 20 includes input device(s) 24, output device(s) 26, and a display device 28. Applicator 22 is attached to an output 29 of control unit 20 via a coupler 30 that may contain one or more couplings.

Applicator 22 may include one or more input devices 49 (FIG. 2), such as a trigger or foot pedal, for activating the delivery of energy. A distal end of applicator 22 may be shaped to laparoscopically or transvaginally access the support structure tissue.

Figure 2:
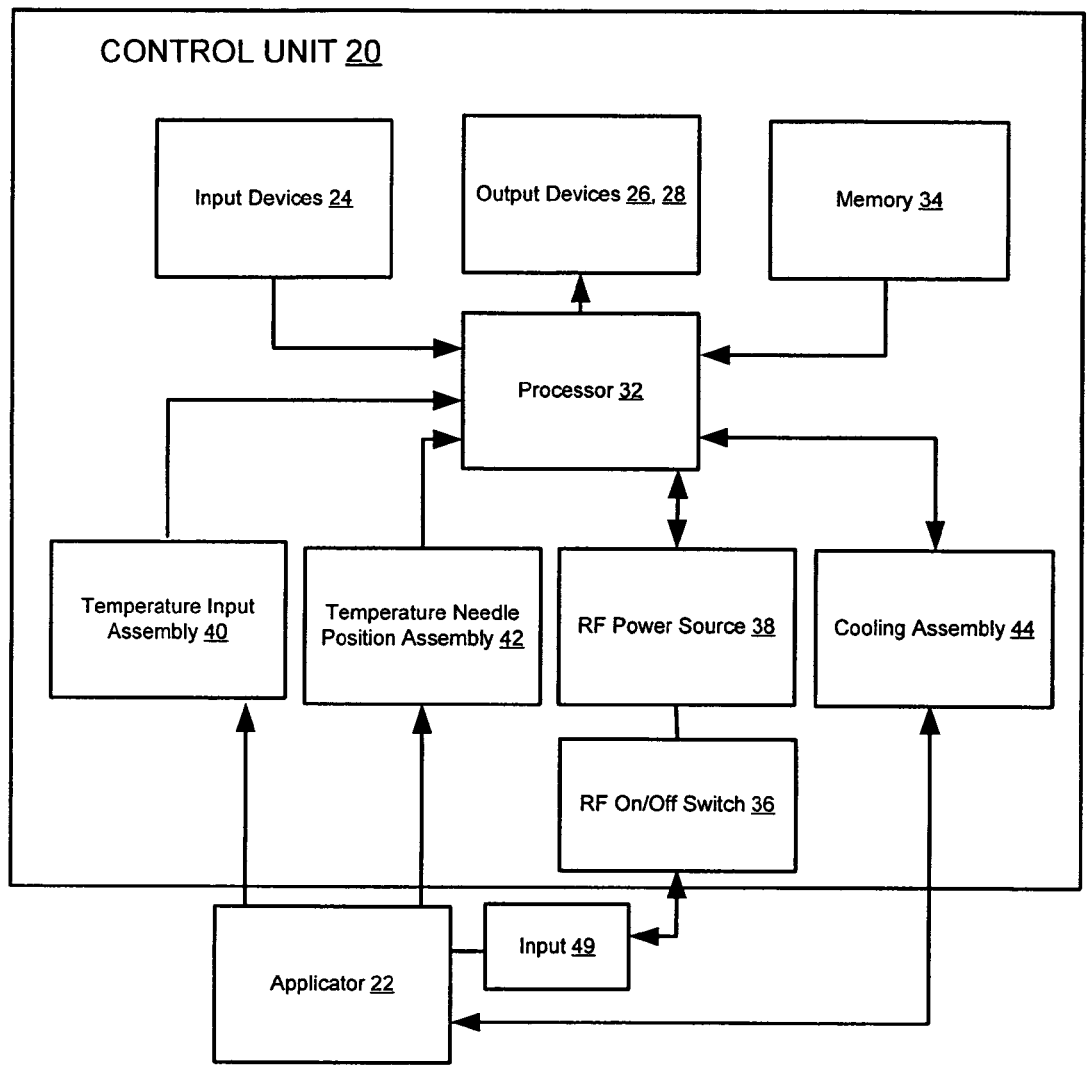
FIG. 2 is a block diagram of a control unit incorporating the principles of the present invention.

FIG. 2 is a block diagram of control unit 20. In preferred embodiments, control unit may be of a size and shape that allows the control unit 20 to be mounted on a standard hospital IV pole. Control unit 20 includes a processor 32 that controls the functionality of control unit 20. Processor 32 has associated therewith a memory 34 adapted to store software code instructions to operate the assemblies in control unit 20 so as to carry out the methods of the present invention. Input devices 24, such as one or more buttons, are coupled to processor 32 to allow a user to input data and instructions into control unit 20. One or more output devices 26, such as a speaker, are coupled to processor 32 to allow audible tones to be output to the user during the procedure to provide treatment information to the user. A display 28 cooperates with processor 32 to provide visual status and error messages pertaining to each step of the process carried out by the present invention.

Control unit 20 includes a switch 36 that serves to activate and deactivate transmission of energy from a power source 38, such as a radiofrequency (RF) power source, to electrodes on applicator 22. Switch 36 may be activated with activation and deactivation of the input device 49 on applicator 22, or the like.

In some embodiments, applicator 22 may also include one or more temperature sensors, such as thermistors or thermocouples, to monitor a treatment tissue temperature. In such embodiments, control unit 20 includes a temperature input assembly 40 for receiving and analyzing the temperature data signals. Optionally, one or more of the temperature sensors may be mounted on a deployable needle assembly for deployment into the target support tissue. In such embodiments, the control of the needle will be controlled by a temperature needle position assembly 42.

A cooling assembly 44 may optionally be coupled to processor 32 and applicator 22 and will be configured to pre-cool the tissue contacted by applicator and/or cool the tissue during the delivery of the energy. A more complete description of some examples of cooling assembly 44 are described in commonly owned U.S. Pat. Nos. 6,091,995 and 6,480,746, the complete disclosures of which are incorporated herein by reference. As can be appreciated, cooling assembly 44 is optional and not all applicators of the present invention include cooling assembly 44.

One useful embodiment of the control unit will now be described. Processor 32 may identify and display appropriate error messages pertaining to the following conditions: cooling assembly does not reach appropriate temperature in prescribed time, coolant flow rate out of range, coolant conductivity out of range, errors encountered during the diagnostic system tests, and the like. Some embodiments of processor 32 allow the user to set date and time, audio tone level, language selection for display on display device 28, power levels, desired temperature goals, desired time ranges, and the like. Processor 32 generates audio tones to prompt the user for actions and to indicate error and out of range conditions. A continuous or intermittent audio tone may be emitted by a speaker 26 associated with processor 32 at a steady rate when RF energy is applied. Processor 32 may generate a welcome screen showing a logo or other graphics desired by user of system 10. Processor 32 may display recoverable error condition messages and prompts the user to correct the cause. Unrecoverable error messages may be displayed on display device 28 and give appropriate error information.

Control unit 20 may be configured to complete a self-test each time the power is turned on. Control unit 20 allows processor 32 to complete its internal tests and display error messages accordingly. A fault in the RF output test can be diagnosed and displayed as an error condition. Processor 32 may be programmed to provide a clock signal for hardware detection of software operation. Processor 32 performs tests of internal subsystems, including but not limited to the analog and digital electronics. Control unit 20 provides a special test, diagnostics and service mode, which will allow the manufacturer or servicer of system 10 to bypass the normal diagnostic self-tests, be able to manually execute all functions and perform calibration and setup. This mode is generally not be accessible to the user.

Figure 2A:
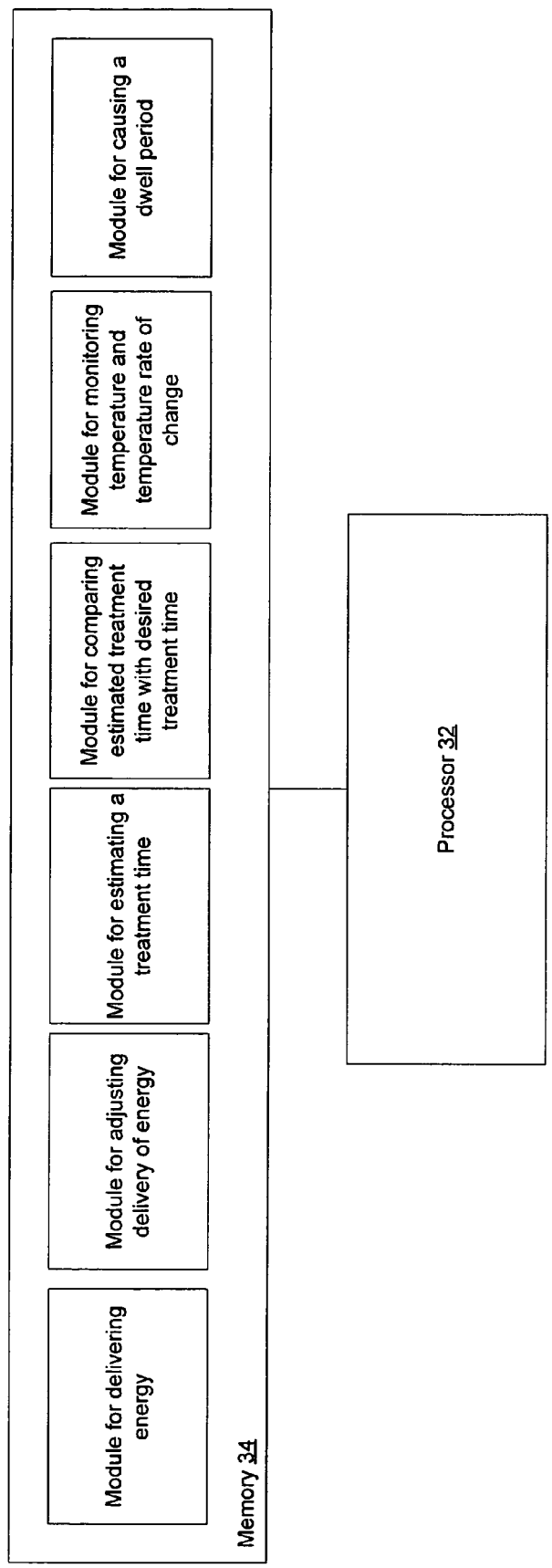
FIG. 2A illustrate code modules that may be incorporated into a memory of the present invention.

FIG. 2A schematically illustrates code modules that may be stored in the memory 34 and processed by processor 32. A more complete description of the functionality of the code modules will be described below in relation to the methods of the present invention.

Figure 3A:
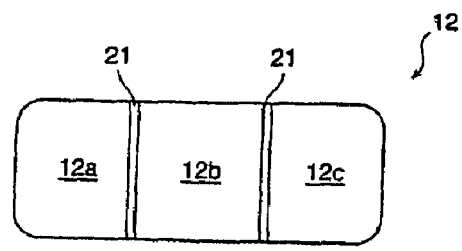
FIG. 3A shows a cooled surface applicator with three active electrodes and insulators between the electrodes.
Figure 3B:
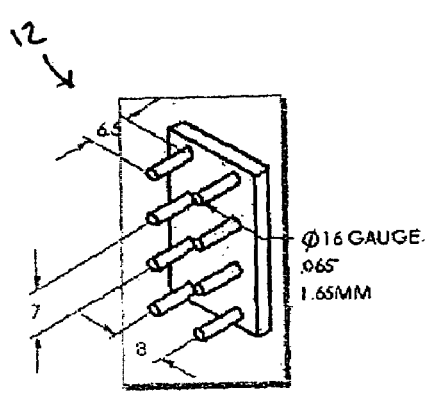
FIGS. 3B to 3E illustrate some needle electrodes and blade electrode assemblies that are encompassed by the present invention.
Figure 3C:
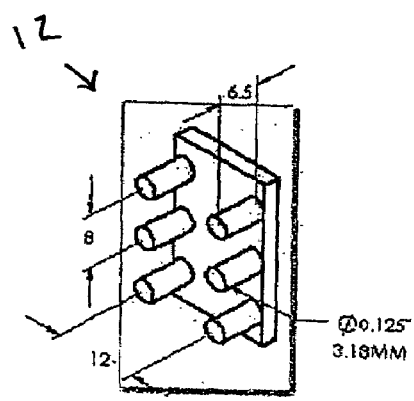
Figure 3D:
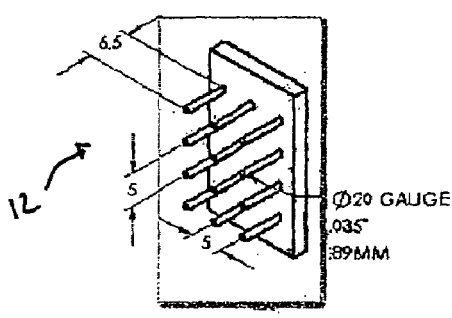
Figure 3E:
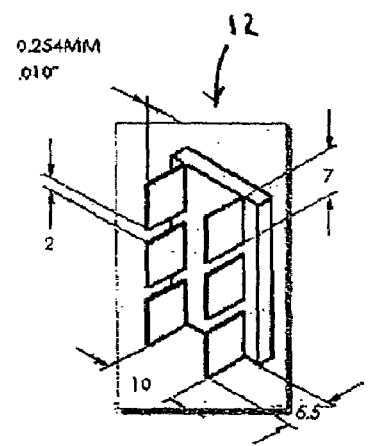
Figure 3:
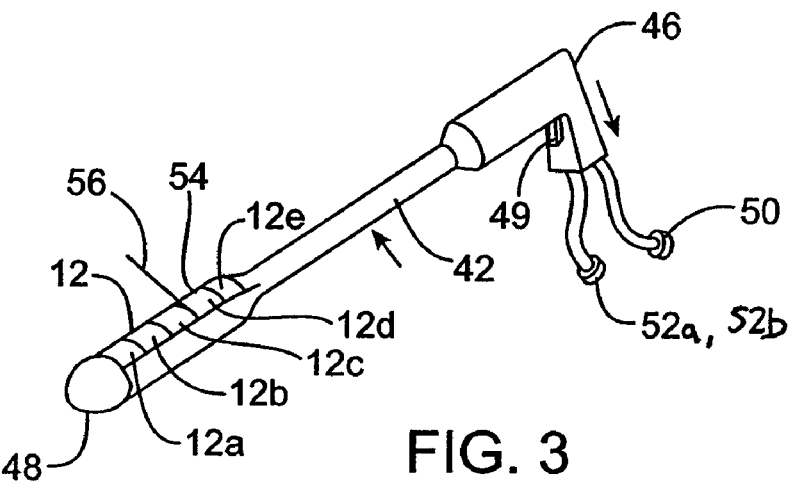
FIG. 3 is a perspective view a cooled surface applicator incorporating further principles of the present invention.

FIG. 3 is a detailed perspective view of another embodiment of an applicator that is encompassed by the present invention. The applicator has a proximal end 46 and a distal end 48. One or more input devices, such as a footswitch (not shown) or trigger 49, may be coupled to applicator and in communication with switch 36 (FIG. 2) to control the delivery of energy through applicator 22. Electrode 12 (including segments 12a, 12b, 12c, 12d, and 12e) is mounted at or near the distal end 48 of applicator 22 to deliver the energy to the tissue. While five electrode segments are illustrated, it should be appreciated that any number of electrode segments may be used. For example, in other embodiments there may be a single pair of electrodes. As shown in FIG. 3A, other embodiments of applicator 22 may have a three-electrode configuration 12a, 12b, 12c, that are separated by insulators 21. Further alternate embodiments of the electrodes 12 are shown in FIGS. 3B to 3E and include needle electrodes or blade electrode assemblies. A more detailed description of some other electrode configurations may be found in commonly owned U.S. patent application Ser. No. 60/440,711, filed Jan. 16, 2003 and entitled "Non-Surgical Incontinence Treatment System and Method, the complete disclosure of which is incorporated herein by reference. As can be appreciated, the electrode assemblies illustrated herein are merely illustrative, and are not meant to limit the scope of the present invention.

Applicator 22 may take on a variety of different sizes and shapes. In the non-invasive cooled electrode embodiment shown in FIG. 3, applicator 22 preferably has a diameter of between about 2 cm and about 4 cm, a treatment surface that has a width between 2 cm and 3 cm and a length between about 3 cm and about 5 cm long, and a shaft length of between about 6 cm and about 12 cm. In one configuration of the embodiment of FIG. 3A, the treatment surface is 25 mm wide by 39 mm long and has 1 mm long insulators 21 between the electrodes 12a, 12b, 12c.

An electrical coupling 50 is coupleable to RF power source 38 of control unit 20. In embodiments which include a cooling assembly, a fluid coupling 52a, 52b provides attachment between the applicator and cooling assembly 44 of control unit 20. Cooling fluid may be recycled through applicator 22 to cool the electrode 12. As such, more than one fluid coupling may be provided (not shown). A more complete description of the cooling assembly of the present invention may be found in co-pending U.S. patent application Ser. No. 10/768,778, filed Jan. 30, 2004 and entitled "Methods and Devices for Controlling a Temperature of an Applicator Body," the complete disclosure of which is incorporated herein by reference.

The segments of electrode 12 are typically quite close to each other, and preferably define a substantially flat electrode surface 54. The cooling fluid or gas may flow immediately below surface 54, with the surface material preferably being both thermally and electrically conductive. Surface 54 is typically as large or larger than the tissue region to be treated, and a thermocouple or other temperature sensor (not shown) may be mounted adjacent or on the surface for engaging the tissue surface so as to measure the temperature of the engaged tissue.

In a preferred embodiment, a temperature probe 56 is attached to applicator 22 and is deployable into a patient tissue target zone using the temperature needle position assembly 42 (FIG. 2). The temperature probe 56 may be in the form of a metal needle with one or more thermocouples located at the needle tip and/or along the shaft of the needle. The needle is designed to penetrate tissue to place the thermocouples in the target support tissue. Alternatively, the temperature probe can be separate from applicator 22. In either case, the temperature probe 56 may be operably coupled to temperature input assembly 40 of control unit 20 (FIG. 2). In the case of the non-cooled multi-electrode applicator the thermocouple may be mounted on the applicator contact surface and may remain in contact with the tissue between the electrodes as it is being heated.

Figure 4:
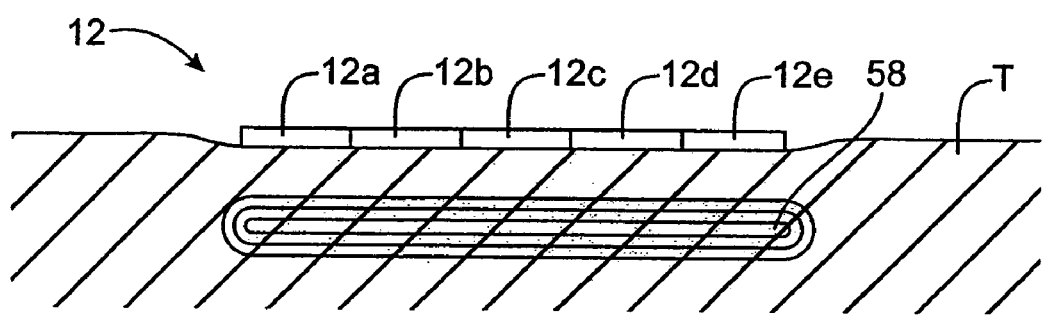
FIG. 4 schematically illustrates the positioning of an electrode of the applicator of FIG. 2 relative to patient tissue T.

FIG. 4 schematically illustrates the positioning of electrode 12 relative to patient tissue during implementation of principles of the present invention. As seen therein, electrode 12 is disposed so as to contact a tissue layer T of a patient body at a position proximal to a target zone 58 within the patient body for which strengthening is desired. Specifically, each of segments 12a, 12b, 12c, 12d and 12e is adapted to contact a corresponding region, disposed between each such electrode segment and target zone 58, of tissue layer T. As noted above, it may be desirable to pre-cool the proximal tissue T prior to delivering energy and/or cool the proximal tissue T during the delivery of energy so as to reduce the heating damage to the proximal tissue T positioned between the cooled electrodes and the target zone 58. Similarly, the three electrode embodiment shown in FIG. 3A will have segments 12a, 12b and 12c in contact with the tissue T so as to treat the target zone 58.

Figure 5:
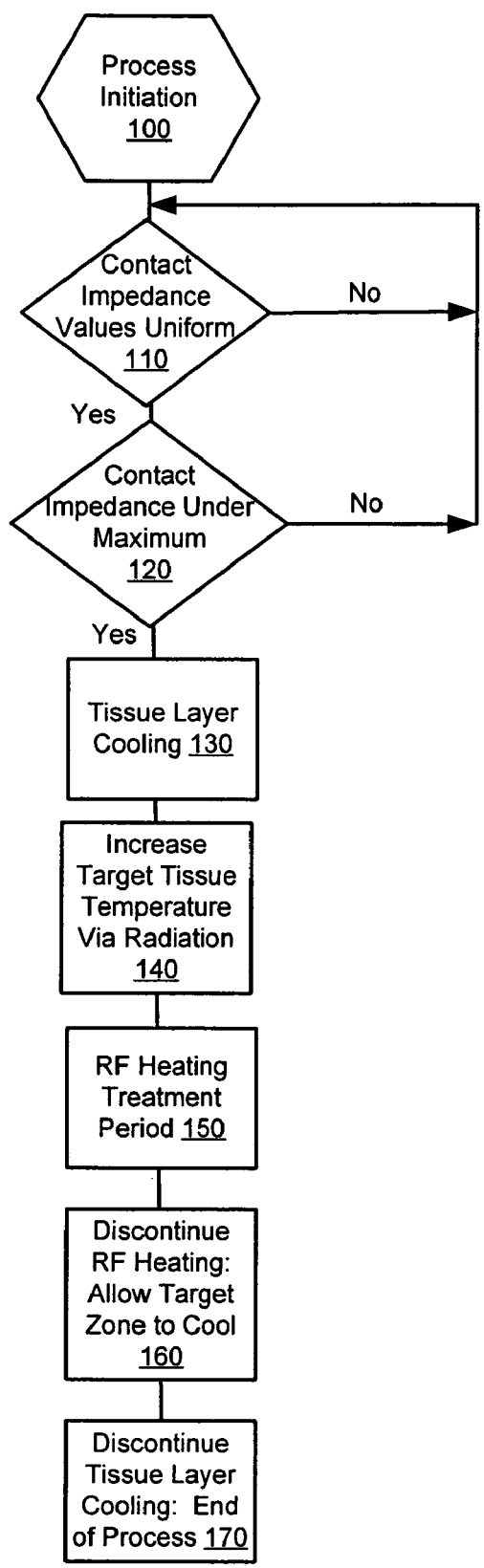
FIG. 5 is a flow diagram illustrating one embodiment of a process through which principles of the present invention are employed in the heating process.

FIG. 5 is a flow diagram illustrating one example of a method through which principles of the present invention are employed in tissue strengthening/contraction/stiffening a support structure tissue of a pelvic support system of a patient for treatment of incontinence using the cooled electrode applicator. As noted above, the methods of the present invention may be carried out with software or hardware modules in control unit 20 that are shown in FIG. 2A. While FIG. 5 illustrates one preferred method, the present invention also encompasses methods that comprise more or less steps than are illustrated.

At step 100, the user may optionally activate a power activation switch of control unit 20. During the initiation, the control unit 20 may prompt the user to enter time parameters, temperature parameters, power parameters, interval parameters, and the like. In some embodiments, such parameters may be preset and the user will not have to input the parameters.

In response to switch activation with the input device 24, processor 32 may perform a diagnostic self test while displaying on display device 28 a system test message showing the progress of the tests. If any component of control unit 20 fails the test, an error code and a description of the failure shall be displayed on display device 28. Optionally, if the diagnostic self test indicates no such error, processor 32 shall provide a message to display device 28 indicating that the cooling assembly 44 is coming down to a predetermined cool-down temperature. This message may further indicate the current temperature of and estimated time to predetermined cool-down temperature of the cooling assembly 44.

Additionally, if the diagnostic self test indicates no such error, processor 32 may provide a message to display device 28 or an audible tone to output device 26 indicating that control unit 20 is ready for attachment of applicator 22 thereto. Upon attachment of applicator 22, processor 32 may also determine whether applicator 22 is operably compatible with control unit 20. Processor 32 may further cause display device 28 to display the status of such compatibility, including any associated error messages. Processor 32 typically continually monitors cooling assembly 44 and causes display of the cooling assembly status.

Once applicator 22 is connected to controller 20, processor 32 may initiate a system test of applicator 22. Such applicator test may include an additional processor (not shown). Display device 28 may prompt the user to advance the temperature probe 56 into the air, retract the temperature probe 56 from the air, and/or press a footswitch (not shown) or other input device 49 coupled to control unit 20 to activate the delivery of RF energy to the applicator electrode 12. Processor 32 may determine the temperature probe state (e.g., advanced or retracted) by comparing measured temperature values to predetermined values that correlate to the temperature of a cooled electrode 12 or the temperature of air in a typical setting. Processor 32 monitors the RF voltage and current values to verify through electrical impedance calculations that electrical continuity exists to the individual elements of electrode 12. Processor 32 may then determine continuity status by comparing calculated impedance values to predetermined values that correlate to continuous or broken electrical connections to the electrode segments. At the conclusion of the applicator test, if an error message is displayed the user may be prompted to correct the errors and re-run the system test. If no errors are indicated, processor 32 generates a message to display device 28 (and/or output devices 26) indicating ready-for-placement status of applicator 22. The process may then move to optional steps 110 and 120.

The user may access the target support tissue and position the applicator against the tissue. For treatment of incontinence, the applicator may access the pelvic support tissue vaginally or laparoscopically. At optional steps 110 and 120, the electrode 12 may be contacted against tissue T and an acceptable or unacceptable contact condition between electrode 12 and tissue layer T may be electronically determined. If the cooled electrode surface 12 does not uniformly contact the tissue surface, the target tissue zone may not be heated adequately and the proximal tissue T interposed between the electrode 12 and target structural support tissue 58 may not be adequately cooled. This may cause inadequate treatment of the target structural support tissue 58 and unintended treatment of the proximal tissue T. The user places the applicator 22 such that electrode 12 contacts the proximal tissue layer T that is adjacent to the target zone 58. The temperature probe 56 is not deployed into the target tissue so that the applicator 22 may be freely repositioned if necessary. Stepping on the footswitch (or activating trigger 49) will cause each segment pairs of electrode 12 to irradiate with energy at a first power level each corresponding region of tissue layer T. Preferably, this first power level is approximately 5 watts and is such that no (or minimal) tissue heating is effected. Specifically in the three electrode case, control unit 20 applies RF energy alternately between the center electrode segment 12b and either the distal electrode segments 12a or proximal electrode segments 12c. Preferably, such energy switching from one electrode segment pair to another occurs approximately every three seconds, but may switch more rapidly to acquire contact condition information more quickly.

At step 110, uniformity of electrode contact can be determined by comparing the difference in tissue electrical impedance measured between the distal/center and proximal/center segments. Tissue contact impedance is measured as the RF is switched from the distal to proximal electrode segments and vice versa after a predetermined time of irradiating the tissue. The maximum impedance difference between the distal and proximal electrode segments is defined as the Tissue Impedance Modulation (TIM). TIM can be computed by processor 32. Preferably, a TIM of greater than 20Ω shall result in processor 32 providing a message to display device 28 warning that the electrode contact to the tissue is unacceptable. A TIM greater than approximately 14Ω to 20Ω shall result in processor 32 providing a message to display device 28 warning that the electrode contact to the tissue is marginal but acceptable. A TIM of 14Ω or less shall result in processor 32 providing a message to display device 28 indicating that the electrode contact to the tissue is acceptable. It should be appreciated however, that the above impedance values are merely examples, and that the impedance values may be adjusted for different tissues and electrode geometries. For example, instead of having the TIM threshold as 20Ω, the TIM can threshold can be anywhere between a range of about less than 15Ω to 30Ω or more. The display of TIM may on display device 28 also be done graphically such as the position of a bar denoting the TIM value and/or encoded by color such as red for unacceptable, yellow for marginal, and green for acceptable.

If the cooled electrode surface contacts the tissue surface uniformly but with inadequate force, the target tissue zone may not be heated adequately and the proximal tissue T interposed between electrode 12 and target tissue may not be adequately cooled. This may cause inadequate treatment of the target tissue and unintended treatment of the proximal tissue. At step 120, processor 32 can determine acceptable contact force by measuring the maximum impedance of both the distal and proximal electrode sets. Preferably, if the maximum impedance exceeds a typical value of between a range of 200Ω to 400Ω, the processor 32 shall provide a message to display device 28 warning that the electrode contact to the tissue is unacceptable. The maximum acceptable value may range from about 200Ω to about 400Ω, depending upon tissue type and electrode geometries.

It should be appreciated that in other exemplary embodiments, if the maximum impedance value exceeds a predetermined value or if the TIM exceeds a predetermined value, instead of a displaying a warning on display device 28, the processor may prevent the processor from moving on to the next step in the method.

In exemplary embodiments, TIM and the maximum impedance values will both be measured. It should be appreciated however, that in alternative embodiments, if desired, only one of TIM and the maximum impedance values will be measured.

Upon determining an acceptable contact condition, if not already deployed, the user may deploy the temperature probe 56 into the tissue. At step 130, tissue may optionally be cooled by the fluid cooling system of applicator 22 so as to cause the temperature of target support tissue 58 to remain below a first predetermined temperature. Cooling the tissue T prior to application of heating energy lowers the temperature of tissue adjacent to the target zone so as to minimize heating of this adjacent tissue due to thermal conduction from the target support tissue as the target support tissue 58 is heated due to resistance to current flow by directed application of RF energy to the target support tissue 58. Processor 32 receives the temperature of the target support tissue 58 as provided by the temperature probe and monitors the progress of cooling. Target support tissue temperature information is sent by processor 32 to display device 28. When the tissue zone 58 has dropped to a pretreatment cool-down temperature of, preferably 30° C. or less (but may range from 25° C. to 35° C.), processor 32 generates a message for display on display device 28 advising the user that RF treatment energy may be applied to target support tissue 58. Processor 32 will prevent RF treatment energy from being applied until the pretreatment cool-down temperature has been reached. It should be appreciated, however, that this pre-heat treatment cooling is optional.

As can be appreciated, depending upon tissue type, desired treatment temperature, treatment time, and the like, other embodiments of the present invention may not provide pre-cooling of the tissue. For example, in some embodiments, electrodes 12 may be contacted directly against the support tissue 58 such that pre-cooling and/or cooling of the electrodes 12 during the treatment is unnecessary.

At 140, the target support tissue 58 may be irradiated by electrode 12 for a finite time period with RF energy so as to increase the temperature of target support tissue 58. When the user activates the RF "On" switch 36, processor 32 may apply the initial RF power. For the non-cooled multi-electrode applicator an initial RF energy of typically 12 Watts to 15 Watts is applied. In the cooled electrode embodiment, the initial power is about 15 Watts to about 25 Watts. In either embodiment, the power is delivered for a fixed amount of time, (preferably 25 seconds ±5 seconds). The value for initial RF power and time of application are selected to provide minimal tissue heating so as to reduce the likelihood of overheating non-target tissue in the event of unacceptable tissue contact. The acceptable contact between applicator 22 and tissue layer T may optionally be confirmed during the heat treatment 140. Contact quality information is shown on display device 28. The user may make use of this information to attempt to improve contact quality if unacceptable or marginal. If at the end of the initial heating period, contact is unacceptable, RF energy application may be ceased. If contact is acceptable, processor 32 may then move to heat treatment 150 for the secondary RF heating treatment period.

A non-cooled, multi-electrode applicator may not have a contactor determination step or two heating steps 140, 150. In such embodiments, heating can start at about 12 Watts to about 15 Watts and then adjustment to the wattage are begun immediately at predetermined intervals during the treatment. Alternatively there may be a specified time period where the adjustment is disabled to allow the initial heating rate spike to pass.

The cooled electrode applicator may have the two step start of heating power and may measure contact between the electrode and tissue. Once contact is determined to be sufficient, there is a further time delay until wattage adjustment begins so as to limit the response to the initial rapid rate of heating.

During heat treatment 150, a variety of power schemes may be used to continue to heat the support tissue 58 to its target temperature. If desired, during heat treatment 150, processor 32 may optionally monitor contact condition throughout the heating period 150. If contact becomes unacceptable during heat treatment 150, RF power may be turned off automatically via a signal generated by processor 32. It should be appreciated however, that in alternative embodiments, instead of turning off the RF power, the RF power may be reduced to a lower power level, until uniformity of contact is again achieved. The lower power level may or may not cause the first tissue layer to be heated.

The user can turn off the RF power at anytime by deactivating the RF On/Off switch 36 through activation of input device 49. The user may pause treatment for, preferably, two to four seconds. Within this time, the user may resume treatment by reactivating RF On/Off switch 36; otherwise, processor 32 shall disable RF treatment power and proceed to step 160.

During heat treatment 150, control unit 20 may employ a single power level heating scheme (e.g., same or different level from heat treatment 140) or an adjustable power level heating scheme to heat the support tissue to the target temperature. In one embodiment, during heat treatment 150, the power level is maintained at a constant power level as heat treatment 140. For example, the power level in steps 140, 150 may be initially maintained at a constant 12 W to 15 W. Such a heat treatment is typically used with the non-cooled multi-electrode embodiment. In other embodiments, the heat treatment 150 is adjusted to a different power level from heat treatment 140. For example, for a cooled electrode applicator, the heat treatment 140 may have a power level of between about 15 W to about 20 W. During heat treatment 150, the power level may be raised to a level between about 30 W and about 40 W. In either embodiment, the tissue temperature and temperature rate of change of target support tissue 58 is monitored throughout the heat treatment 140, 150, as described below.

Figure 6:
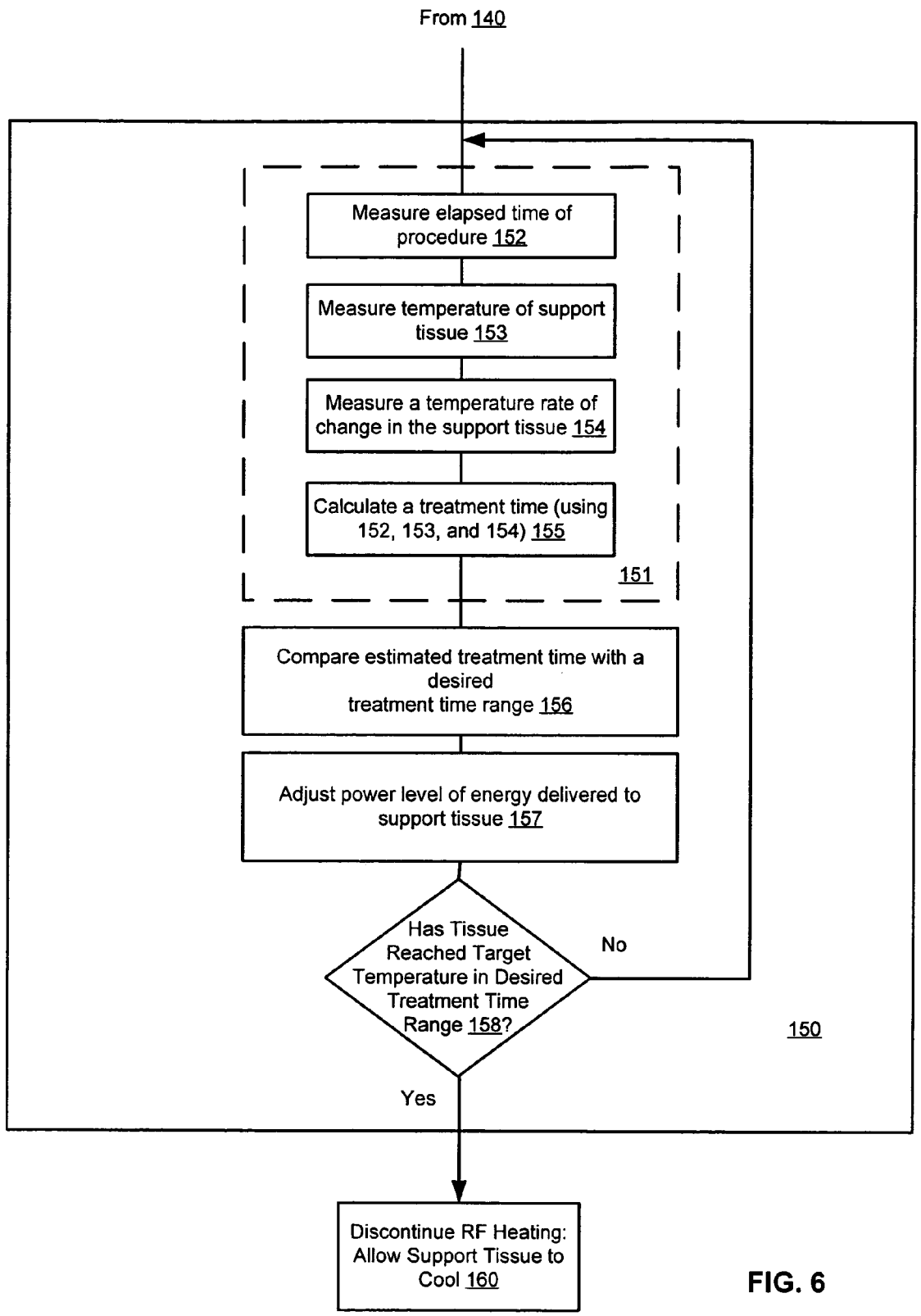
FIG. 6 is a flow diagram illustrating in further detail one embodiment of a heat treatment 150 of the flow diagram of FIG. 5.
Figure 7:
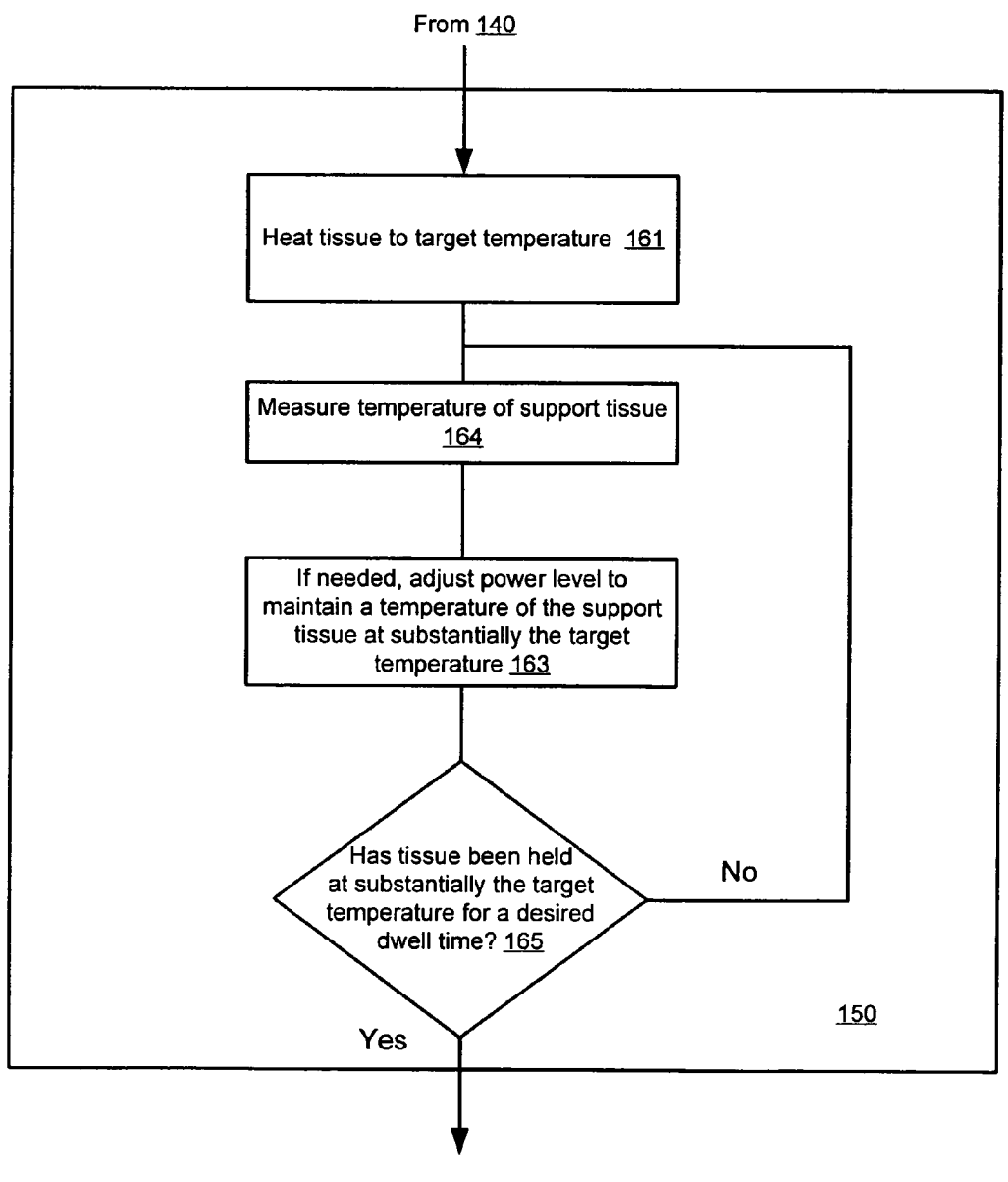
FIG. 7 shows an alternative embodiment of a heat treatment 150 of the flow diagram of FIG. 5.
Figure 8:
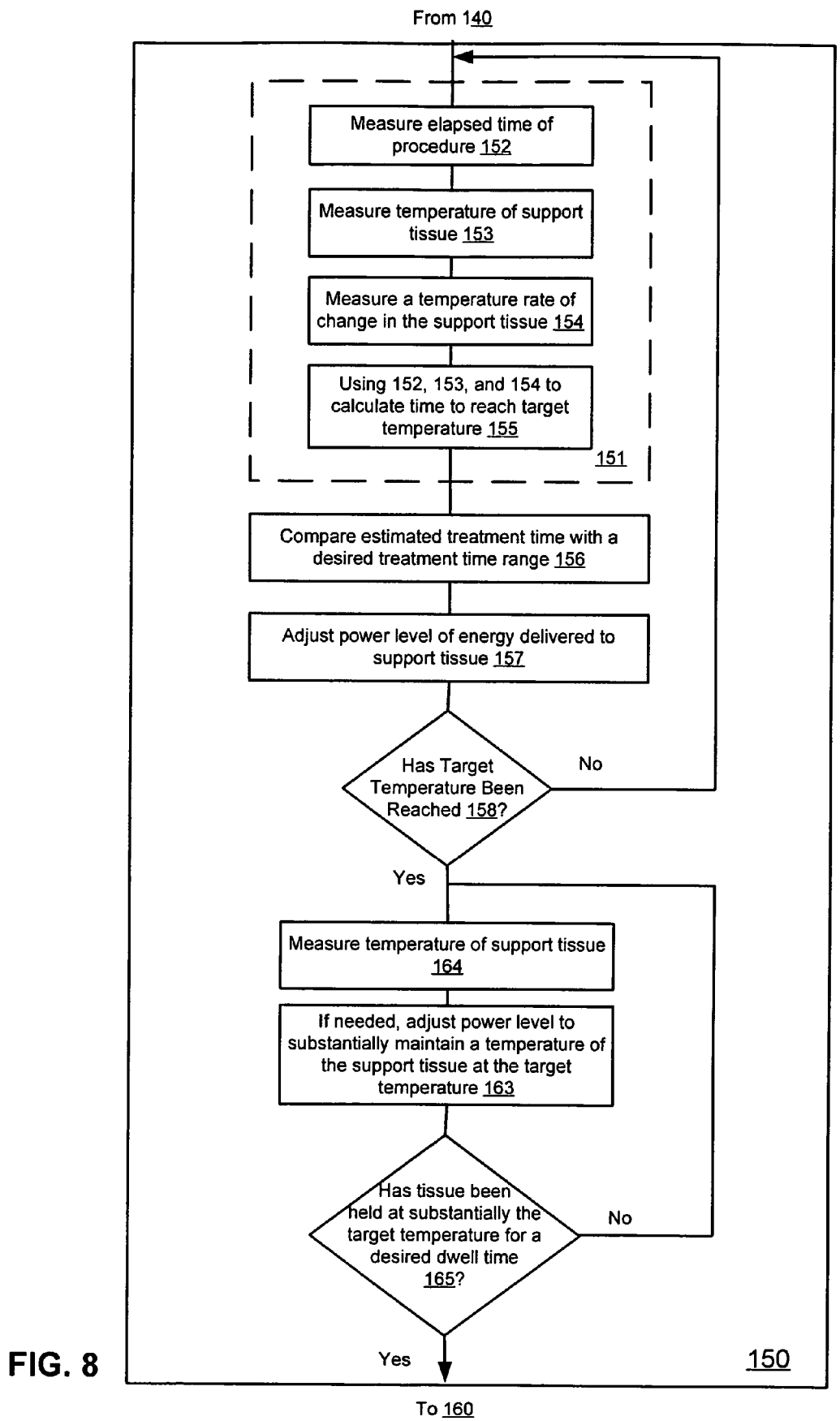
FIG. 8 shows another alternative embodiment of the heat treatment 150 of the flow diagram of FIG. 5.

FIGS. 6 to 8 illustrate some examples of heat treatments 150 that are encompassed by the present invention. For example, upon entering the heat treatment 150, the RF treatment power may be initially adjusted from the first heat treatment 140 power level to a higher power level, adjusted to a lower power level, or the RF power level may initially be held at the same power level as heating stage 140.

As shown in FIG. 6, one embodiment of the secondary heat treatment 150 comprises adjusting a power level of the energy to effect the overall time for reaching the target temperature so that the target temperature is not reached in an excessively long or excessively short time period. In such embodiments, control unit 20 may be programmed to continuously or periodically estimate the time it will take to reach the target temperature 151 (hereinafter referred to as "estimated treatment time" or "ETT"). The estimated treatment time may then be compared to a preselected, desired treatment time range 156 to determine what sort of power adjustments 157 are needed during the heat treatment 150.

In order to estimate the treatment time 151, control unit 20 measures the elapsed time of the treatment 152. Using the temperature probe 56, control unit 20 may also measure the real-time temperature of the support tissue 153 and the temperature rate of change in the support tissue (e.g., temperature slope) 154 over a selected time interval of the heat treatment. Once such parameters have been measured, the estimated treatment time (ETT) may be calculated 155 as follows:

$$ETT = \text{Elapsed Time (seconds)} + \frac{[\text{Target Temperature (° C.)} - \text{Current Temperature (° C.)}]}{\text{Rate of Temperature Change (° C./second)}}$$

In preferred configurations, the current temperature and the rate of temperature change is a smoothed average of the temperature and rate of temperature change over the selected interval, respectively. In one embodiment, the parameters are measured over a selected interval of six seconds. The six second interval is selected because Applicants have found that six seconds is approximately the same time it takes the support tissue to respond to a power level change. As can be appreciated, the selected interval may be different for target tissue structures other than the endopelvic fascia. Smoothing such parameters has been found to reduce the effects of rapid, instantaneous temperature oscillations during the measurements.

The estimated treatment time may then be compared to the desired treatment time 156. If the estimated treatment time is coincident with a desired treatment time range, the power level may be left as is. However, if the estimated treatment time is not coincident with the desired treatment time range, the power level may be adjusted upwards or downwards 157, depending on whether the estimated treatment time is larger (e.g., too slow) or smaller (e.g., too fast) than the desired treatment time.

Figure 6A:
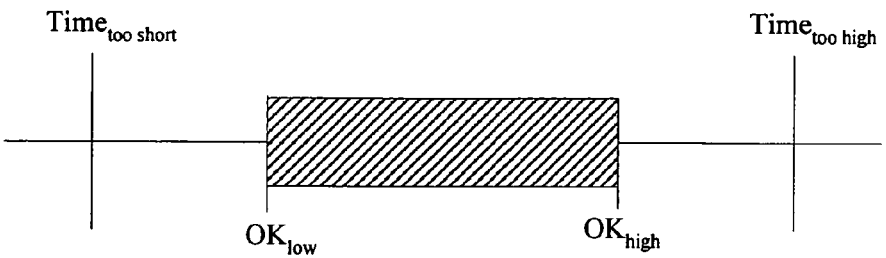
FIG. 6A illustrates four time parameters that are used to adjust the power level during heat treatment 150.

Various methods of adjusting the power level may be used. As shown in FIG. 6A, during the process initiation 100 the user may select, or the control unit may be preprogrammed to define a lower range of the acceptable desired treatment time ($OK_{low}$) and an upper range of the acceptable desired treatment time ($OK_{high}$). If the ETT is not within the desired treatment range, the power level may be increased or decreased in a step-wise manner, depending on if the estimated treatment time is higher than $OK_{high}$ or lower than $OK_{low}$. The step-wise adjustments may be preselected as ±1 Watts or less, ±2 Watts or less, or ±5 Watts or less. As can be appreciated, while such step-wise adjustments are preferred, other adjustment levels may be used without departing from the scope of the present invention.

In other configurations, the amount of power adjustment may be based on the size of the difference between the estimated treatment time and the desired treatment time(s). For example, during process initiation 100, the user may also be prompted to input secondary time parameters in the form of a lower level of treatment time $Time_{TooFast}$ and an upper level of treatment time $Time_{TooSlow}$.

If the ETT is between the $OK_{low}$ and $OK_{high}$, then the power level is maintained at its current level and no power level adjustments are made. If the ETT is between $OK_{high}$ and $Time_{TooHigh}$ or between $OK_{low}$ and $Time_{TooShort}$, the power may be adjusted by a preselected step-wise adjustment (e.g., ±1 Watts or less, ±2 Watts or less, or ±5 Watts or less). If however, the secondary time parameters are used and ETT is less than $Time_{TooSlow}$ or it is higher than $Time_{TooHigh}$, the power level may be adjusted by some multiplier of the preselected step-wise adjustment (e.g., two times, three times, or the like) or by some other selected amount so that gross errors between the ETT and the desired treatment time may be compensated for quickly.

Referring again to FIG. 6, after the power level has been adjusted, control unit 20 continues to monitor the temperature and determines if the tissue has reached its target temperature in the desired treatment time range 158. At any time when the smoothed target temperature is reached, RF power either ends or if dwell is desired (described below), the control 20 transitions to the dwell phase. If the target temperature has been reached in substantially the desired treatment time range (and no dwell is desired), then the method moves onto Step 160 where the RF heating is discontinued so as to allow the support tissue to cool. If the target temperature has not been reached, control unit 20 may repeat steps 151, 156, 157, until the target temperature has been reached in the substantially the desired treatment time range.

While not illustrated, in most embodiments, there is an overriding time limit (e.g., Maximum Treatment Time) which will discontinue RF treatment if the total elapsed RF treatment time exceeds this value. This will end RF treatment even if target temperature has not been achieved or even if the desired dwell time has not been achieved. Maximum treatment time is constrained to be greater than the setting for the desired rise time.

FIG. 7 illustrates an alternative embodiment of a heating treatment period 150 that incorporates a dwell time. In the embodiment illustrated in FIG. 7, any conventional or proprietary method may be used to heat the tissue to a first target temperature 161 (e.g., constant energy level, two-stage energy level, or adjustable power level (described above)). One potential power scheme to heat the tissue to the target temperature is describe in commonly owned, copending U.S. patent application Ser. No. 10/102,596, filed Mar. 19, 2002 (issued Apr. 19, 2005 as U.S. Pat. No. 6,882,885), the complete disclosure of which is incorporated herein by reference.

Once the first target temperature is reached, instead of stopping the heat treatment, the tissue is heated in a manner that maintains the tissue at substantially a second target temperature for a predetermined amount of time (hereinafter referred to a "dwell"). The first and second target temperatures may be substantially equal to each other, or the first and second target temperatures may be different from each other. The entry into the dwell period typically involves a reduction in power level from the power level that was used to raise the tissue temperature. This reduction may either be by a constant amount or by an amount of power which is proportional to the rate of heating (temperature slope) at the point when dwell begins.

The power level may be adjusted (upward or downward) one or more times during the dwell period so as to maintain the support tissue at substantially the target temperature for the desired time period. Before, after, continuously during the delivery of energy, or at selected intervals during the delivery of energy, the temperature of the support tissue may be measured to determine the temperature and the effect of the change in the power level on the temperature of the support tissue 164. After the temperature measurement and the change in the level of the power level are made, control unit 20 determines if the tissue has been held at substantially the target temperature for the desired dwell time 165.

If the tissue has been held at the dwell time for the desired time, the power delivery is discontinued and the tissue is allowed to cool 160. If the dwell time has not been reached, the temperature is continued to be monitored and if the tissue temperature is not within the desired temperature range, the process is repeated and the power level is adjusted 163. Applicants have found that oftentimes only one adjustment in the power level during heat treatment 150 is needed to maintain the temperature of the tissue within the desired range. But other times, a plurality of power level adjustments may be made.

FIG. 8 illustrates yet another method encompassed by the present invention. Similar to the embodiment of FIG. 6, control unit 20 may be programmed to continuously or periodically estimate the time it will take to reach the target temperature 151. The estimated treatment time may then be compared to a preselected, desired treatment time range 156 to determine what sort of power adjustments 157 are needed.

In order to estimate the treatment time, control unit 20 may measure the elapsed time of the treatment 152. Using the temperature probe 56, control unit 20 may also measure the temperature of the support tissue 153 and the temperature rate of change in the support tissue (e.g., temperature slope) 154 over a selected interval of the heat treatment. As described above, using the elapsed time, current temperature and the temperature rate of change, the control unit 20 determines the estimated time to reach the target temperature.

The estimated treatment time may then be compared to the desired treatment time 156. If the estimated treatment time is coincident with a desired treatment time range, the power level may be left as is. If the estimated treatment time is not coincident with the desired treatment time range, the power level may be adjusted upwards or downwards 157, depending on whether the treatment time is larger (e.g., too slow) or smaller (e.g., too fast) than the desired treatment time. As is described above, various methods of adjusting the power level may be used.

After the power level has been adjusted, control unit 20 determines of the tissue has reached its target temperature in the desired treatment time range 158. If the target temperature has not been reached, control unit 20 may repeat steps 151, 156, 157, so that the target temperature will be reached in substantially the desired treatment time range. If the target temperature has been reached in substantially the desired treatment time range, then the method moves to the dwell time at step 163.

At 163, the power level may be adjusted (upward or downward) one or more times during the dwell period so as to maintain the support tissue at substantially the target temperature for the desired time period. Before, after, continuously during the delivery of energy, or at selected intervals during the delivery of energy, the temperature of the support tissue may be measured 164 to determine the temperature of the tissue and the effect of the change in the power level on the temperature of the support tissue. After the temperature measurement and the change in the level of the power level are made, control unit 20 determines if the tissue has been held at substantially the target temperature for the desired dwell time 165.

If the tissue has been held at the dwell time for the desired time, the power delivery is discontinued and the tissue is allowed to cool 160. If the dwell time has not been reached, the temperature is continued to be monitored and if the tissue temperature is not within the desired temperature range, the process is repeated and the power level is adjusted 163 to maintain the desired temperature and the heating is continued until the desired dwell time has been reached. After the desired dwell time has been reached the RF heating is discontinued and the tissue is allowed to cool 160.

Referring again to FIG. 5, after any of the heating treatments 150 of FIGS. 6 to 8 are complete, the RF heating is discontinued 160. The target support tissue 58 may be cooled to a predetermined temperature, typically between approximately 30° C. to approximately 50° C. Cooling of the target support tissue and adjacent tissues with cooling assembly 44 after heating reduces the undesirable additional heating of adjacent tissues due to thermal conduction from the target support tissue 58. Upon target support tissue 58 reaching this predetermined temperature, at step 170, cooling of the tissue is discontinued, thus ending the round of treatment. It should be appreciated however, that the post heating cool down cycle is optional, depending upon application such as tissue type, desired treatment temperature, treatment time, and the like.

According to principles of the preferred embodiment of the present invention, the above-described treatment process may be carried out automatically by the system 10 so that the user is relieved of manually adjusting power, etc. The user may turn the RF power on and off and deploy and retract the temperature probe. Processor 32 may maintain the proper power level, monitor the above-described treatment parameters, adjust the power levels (if needed), prompt the user, and display status messages, alerts/warnings and error conditions. These functions, including all associated with the inventive process described above, are typically initiated and/or performed by the above-referenced software code stored in a memory of and executing on processor 32.

EXAMPLES

The following description provide some specific, non-limiting examples that are encompassed by the present invention.

Figure 9:
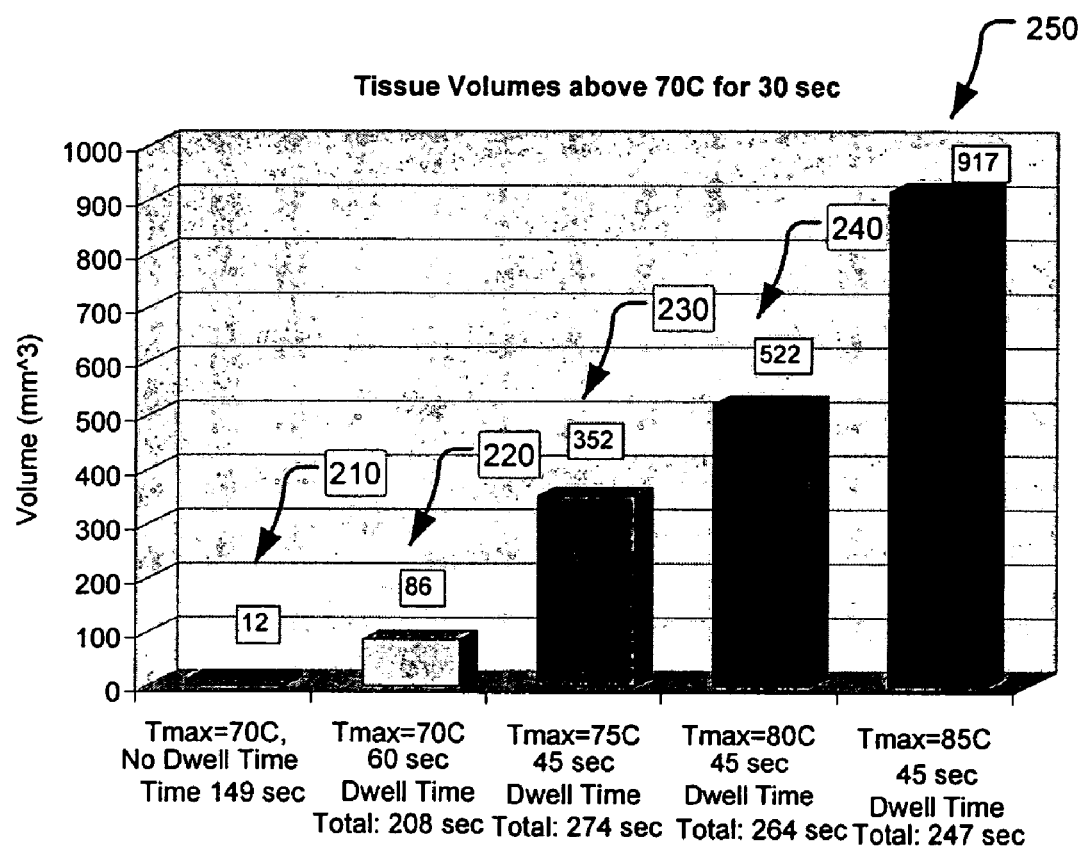
FIG. 9 illustrates a graph which compares tissue volumes that are above 70° C. for 30 seconds which are produced by various heating schemes.

Applicants have found that heating a volume of tissue to a temperature for above 70° C. and dwelling the tissue above 70° C. for more than 30 seconds provides improved incontinence treatment over incontinence treatments that heat to 70° C. and do not provide a dwell time. FIG. 9 is a graph 200 that schematically illustrates tissue volume that is held above 70° C. for various heating treatment schemes of the present invention. The first column 210 shows a heat treatment where energy is delivered to raise the temperature of a thermocouple within a needle at the middle of the treatment zone (about 4.5 mm below the vaginal mucosal surface) to 70° C. in whatever time it naturally takes. The temperature in the middle of the treatment zone is typically the maximum temperature achieved anywhere in the tissue. Once the support tissue hits the target temperature of 70° C., the heat treatment was immediately stopped. Such a treatment provides only a collagen tissue shrinkage volume of 12 mm$^3$ that stays above 70° C. for at least 30 seconds.

In the second column 220, the support tissue was heated to 70° C. and then subjected to a dwell period of 60 seconds at 70° C. For such a heat treatment, the resultant tissue volume was raised by about a sevenfold factor to a collagen tissue shrinkage volume of 86 mm$^3$. Applicants believe that this increased tissue volume relates to the heat spreading out from the hot spot to encompass more tissue.

In the third column, the support tissue was raised to 75° C. prior to a 45 second dwell period, and such heating produced a collagen tissue shrinkage volume of 352 mm$^3$. Applicants believe that this further four fold increase was caused by the fact that the hot spot itself was raised to 75° C. which naturally produces an even larger tissue volume in excess of 70° C.

In the fourth column 240, the tissue was raised to 80° C. prior to a 45 second dwell period, and such heating produced a tissue volume of 522 mm$^3$.

Finally, in the fifth column 250 the tissue was raised to 85° C. prior to a 45 second dwell period, and such heating produced a tissue volume of 917 mm$^3$. Applicants prefer that the heat treatment power scheme produce a volume of 300 mm$^3$ or more, but other tissue volumes may be used, if desired.

Heating the volume of tissue to 70° C. and maintaining the tissue at that temperature for 30 seconds causes shrinkage of 40%, which is about 65% of the maximum amount of the potential tissue shrinkage. See Chen et al., Transactions of the ASME, Volume 119, pp. 372-378 (1997), the complete disclosure of which is incorporated herein by reference. At 75° C. the same tissue shrinkage may be reached in 10 seconds. The selection of an arbitrary "rule" of 70° C. treatment volumes for 30 seconds is a convenient target for the treatment prescription. On one hand, the selection of 75° C. for 10 seconds or even 80° C. for 1 second might be equivalent to heating at 70° C. for 30 seconds, but to get the patient to these higher temperatures runs a greater risk of dangerous temperatures spreading to damage nearby nerves or other sensitive structures. On the other hand, if the method were to select 65° C. for 160 seconds would require the physician to continue treatment for an uncomfortably long time period since it typically requires 100 to 150 seconds with the applicator to reach the target temperature in the first place.

In one test, the power was held constant at 20 W for 24 seconds, and the power was increased to a constant 35 W until the tissue temperature reached the target temperature (e.g., 70° C.), the average time to reach the target temperature was 110 seconds with a standard deviation of 29 seconds. The large standard deviation in time is influenced by differences in power delivery as a result of applicator placement in the body, the level of perfusion (e.g., blood flow), patient to patient anatomical variations and the variants in effectiveness of a vasoconstrictor. The vasoconstrictor maybe used to try to limit perfusion effects, and thus ensure that the target treatment could be reached in the desired time. Some methods of using a vasoconstrictor for the treatment of incontinence is described in commonly owned U.S. patent application Ser. No. 10/029,000, filed Dec. 20, 2001 (issued Jan. 11, 2005 as U.S. Pat. No. 6,840,954), the complete disclosure of which is incorporated herein by reference.

In contrast, using the methods of the present invention, prior to delivery of energy, the user can set the $OK_{high}$ time to be 181 seconds and the $OK_{low}$ time to be 179 seconds (in which the desired overall treatment is 180 seconds to reach the target temperature), the temperature was allowed to be adjusted every six seconds, and the hot spot target temperature was set to be between 74° C. and 75° C.

The power was held constant at 20 Watts for 24 seconds. The power was then increased to 35 Watts for a period of about 30 seconds. To compensate for any difference between the calculated ETT and the preselected desired treatment time, the power was allowed to be adjusted every six seconds (up to a maximum of 40 Watts and down to a minimum of 25 Watts). Applicants found that, on average the power scheme of the present invention reached the target temperature in 169 seconds with a standard deviation of only 10 seconds.

As can be appreciated, the power levels and treatment times will vary depending on whether a cooling assembly is used. For example, the total treatment time for an applicator with a cooling assembly will typically be in the range from about 150 to about 240 seconds, while the total treatment time for the non-cooled multi-electrode device will be in the range from 130 to 200 seconds. This applies to treatment of the endopelvic fascia. Other treatment target tissues may require different treatment time targets.

Figure 10:
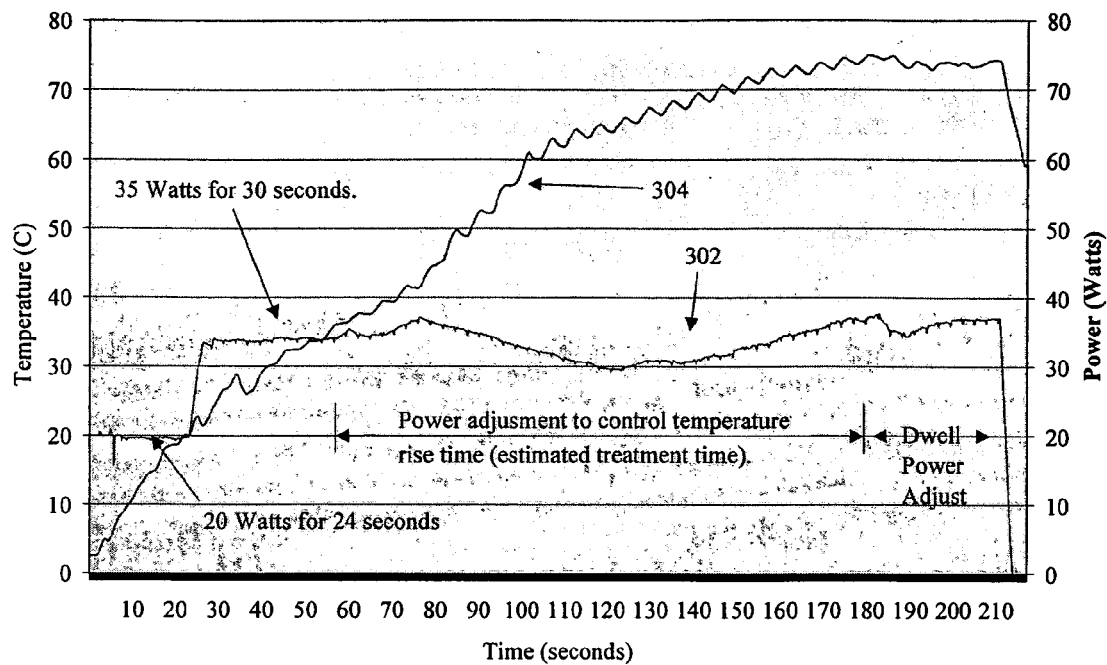
FIG. 10 is a graph which illustrates a power level during heating and a power level during dwell for the non-invasive cooled electrode device.

FIG. 10 illustrates the temperature of the tissue and the corresponding power levels of one test run. The power level graph 302 shows an initial power level of approximately 20 Watts for the first 24 seconds, thereafter, the power is increased to approximately 35 Watts for 30 seconds and then adjusted in a stepwise manner based on the comparison of the ETT with the desired temperature range (in this example $OK_{low}$=179 seconds and $OK_{high}$=181 seconds). A dwell time target was 30 seconds. The dwell started at about 180 seconds and continued until 210 seconds. As shown by graph 302, the power level was dropped down from about 37 W to a lower power level during the dwell period and was continuously adjusted during the dwell period. The drop in power at the beginning of the dwell period may be a fixed value but has been found to provide more consistent values of temperature during dwell if the amount of drop is proportional to the tissue heating rate when the dwell period begins. A typical value for endopelvic tissue might be a drop of 1 Watt for every 0.04° C./second of tissue temperature rise just prior to dwell. As shown by temperature graph 304, the temperature stabilized at about 74° C. during the dwell period. In the illustrated example, the temperature is typically held to within ±1.0° C. of the target temperature.

Figure 11:
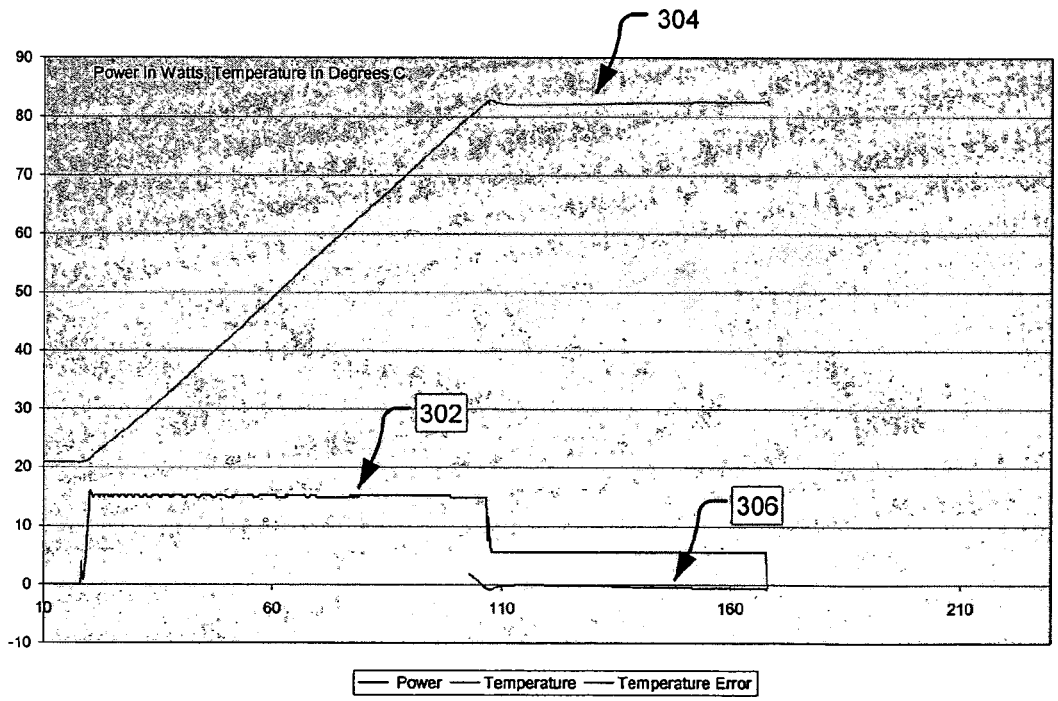
FIG. 11 illustrates a single power drop to maintain the target support tissue at substantially the target temperature for the multi-electrode applicator.

As shown in FIG. 11, for the non-cooled multi-electrode applicator, during the dwell period it may be possible to provide a single adjustment to the power level to substantially maintain the dwell temperature. As shown in FIG. 11, in another test run, the power level 302 is dropped from about 15 W and held constant at a constant 8 W and the temperature was substantially maintained at 82° C., with a temperature error 306 of only about ±0.7° C. of the target temperature. As can be appreciated, in some cases, it may only be required to adjust the power level is small steps, typically 0.5 Watts to about 1 Watt to hold the tissue temperature of within ±0.3° C. of the target value.

Although the invention has been described in terms of the illustrative embodiment, it will be appreciated by those skilled in the art that various changes and modifications may be made to the illustrative embodiment without departing from the spirit or scope of the invention. It is intended that the scope of the invention not be limited in any way to the illustrative embodiment shown and described but that the invention be limited only by the claims appended hereto.

What is claimed is:

1. A method of therapeutically heating a collagenous structural support tissue of a pelvic support system to a target temperature, the method comprising: delivering energy to the structural support tissue; monitoring the effect of the delivery of energy on the structural support tissue to estimate a treatment time of reaching the target temperature; comparing the estimated treatment time with desired treatment time(s); adjusting a power level of the energy if the estimated treatment time is not coincident with the desired treatment time(s).

2. The method of claim 1 wherein monitoring the effect of the delivery of energy comprises: measuring an elapsed time of delivery of the energy to the structural support tissue; measuring a temperature of the tissue and a temperature rate of change of the structural support tissue; and using the elapsed time of delivery of the energy, measured temperature of the structural support tissue, and temperature rate of change at the structural support tissue to calculate the estimated treatment time.

3. The method of claim 2 wherein measuring the temperature and the temperature rate of change at the structural support tissue is carried out only after a predetermined amount of time after commencement of a delivery of energy to the structural support tissue.

4. The method of claim 3 wherein the predetermined amount of time is between approximately 25 seconds and 45 seconds.

5. The method of claim 2 wherein measuring the elapsed time, temperature of the structural support tissue, and the temperature rate of change at the structural support tissue is repeated at predetermined intervals during the delivery of the energy.

6. The method of claim 2 wherein the measured temperature of the structural support tissue and temperature rate of change of the structural support tissue is an average temperature and average temperature rate of change over a predetermined interval.

7. The method of claim 6 wherein the predetermined interval is approximately six seconds.

8. The method of claim 7 wherein adjusting the power level is carried out after each predetermined interval.

9. The method of claim 1 wherein if the estimated treatment time is less than the desired treatment time(s) then the adjusted power level is lower than an original power level.

10. The method of claim 1 wherein if the estimated treatment time is greater than the desired treatment time(s) then the adjusted power level is higher than an original power level.

11. The method of claim 1 wherein adjusting the power level comprises adjusting the power level in step-wise adjustments of .+-.1 Watts, .+-.2 Watts, or .+-.5 Watts.

12. The method of claim 11 wherein a size of the step-wise adjustment is selected based on the difference between the estimated treatment time and the desired treatment time.

13. The method of claim 1 wherein the target temperature is between approximately 65° C. and 75° C.

14. The method of claim 1 wherein the desired treatment time is between approximately 150 seconds and approximately 240 seconds.

15. The method of claim 1 wherein adjusting is automatically carried out by software in a control system memory.

16. The method of claim 1 wherein the structural support tissue is a collagenated tissue in an endopelvic fascia.

17. The method of claim 1 further comprising accessing the structural support tissue transvaginally.

18. The method of claim 1 further comprising accessing the structural support tissue laparoscopically.

19. A system for delivering energy to a collagenous structural support tissue of a pelvic support system, the system comprising: a processor; a memory coupled to the processor, the memory configured to store a plurality of code modules for execution by the processor, the plurality of code modules comprising: a code module for delivering energy to the structural support tissue; a code module for estimating a treatment time of reaching a target temperature; a code module for comparing the estimated treatment time with desired treatment time(s); and a code module for adjusting the delivery of the energy to an adjusted power level if the estimated treatment time is not coincident with the desired treatment time(s).

20. The system of claim 19 wherein the code module for estimating the treatment time of reaching the target temperature comprises: a code module for measuring an elapsed time of delivering energy to the structural support tissue; a code module for measuring a temperature and a temperature rate of change at the structural support tissue; and a code module for using the measured elapsed time, measured temperature and temperature rate of change to calculate an estimated treatment time.

21. The system of claim 19 further comprising a power supply coupled to the processor.

22. The system of claim 21 further comprising an applicator coupleable to the power supply for delivering the energy to the structural support tissue.

23. A method of therapeutically heating a collagenous structural support tissue of a pelvic support system, the method comprising: delivering energy to raise a temperature of the structural support tissue to a first target temperature; and dynamically adjusting a power level of the energy after the structural support tissue has substantially reached the first target temperature so as to allow the structural support tissue to dwell at substantially a second target temperature for a desired amount of dwell time.

24. The method of claim 23 wherein adjusting the power level comprises making an adjustment of the power level upon entry into dwell which is either a constant value drop from an entry power level or a power level drop which is proportional to a rate of change of the tissue temperature at an entry point into the dwell.

25. The method of claim 23 wherein the first target temperature is substantially equal to the second target temperature.

26. The method of claim 23 wherein the first and second target temperatures are between approximately 70° C. and approximately 75° C.

27. The method of claim 23 wherein the desired amount of dwell time is at least approximately 30 seconds.

28. The method of claim 23 wherein the desired amount of dwell time is between approximately 20 seconds and approximately 45 seconds.

29. The method of claim 23 wherein adjusting the delivery of energy comprises reducing a power level of the delivery of energy at least once during the dwell time.

30. The method of claim 23 further comprising: measuring a temperature of the structural support tissue at selected intervals during the dwell time; and further adjusting delivery of energy to the structural support tissue if the measured temperature of the structural support tissue is not within an acceptable range from the second target temperature.

31. The method of claim 23 wherein further adjusting delivery of energy comprises raising or lowering the power level less than approximately 2 Watts.

32. A system for delivering energy to a structural support tissue of a pelvic support system, the system comprising: a processor; a memory coupled to the processor, the memory configured to store a plurality of code modules for execution by the processor, the plurality of code modules comprising: a code module for delivering energy to the structural support tissue at a first target power level; a code module for estimating a treatment time of reaching a first target temperature; a code module for comparing the estimated treatment time with desired treatment time(s) for reaching the first target temperature; a code module for adjusting the delivery of the energy to an adjusted power level if the estimated treatment time is not coincident with the desired treatment time(s), wherein the adjusted delivery of energy is sufficient to cause the first target temperature to be reached in substantially the desired treatment time(s); and a code module for dynamically adjusting a power level of the energy after the structural support tissue has substantially reached the first target temperature so as to allow the structural support tissue to dwell at substantially a second target temperature for a desired amount of dwell time.

33. The system of claim 32 further comprising a power supply coupled to the processor.

34. The system of claim 33 further comprising an applicator coupleable to the power supply for delivering the energy to the tissue.

35. A method of treating a tissue of structural support tissue of a pelvic support system, the method comprising: delivering energy to the structural support tissue at a first power level; estimating a treatment time of reaching a first target temperature; comparing the estimated treatment time with desired treatment time(s) for reaching the first target temperature; adjusting the delivery of the energy to an adjusted power level if the estimated treatment time is not coincident with the desired treatment time(s), wherein the adjusted delivery of energy is sufficient to cause the first target temperature to be reached in substantially the desired treatment time(s); and dynamically adjusting a power level of the energy to a modified power level after the structural support tissue has substantially reached the first target temperature so as to allow the structural support tissue to dwell at substantially a second target temperature for a desired amount of dwell time.

* * * * *

UNITED STATES PATENT AND TRADEMARK OFFICE
CERTIFICATE OF CORRECTION

PATENT NO. : 7,251,531 B2 Page 1 of 1
APPLICATION NO. : 10/768780
DATED : July 31, 2007
INVENTOR(S) : Oren A. Mosher et al.

It is certified that error appears in the above-identified patent and that said Letters Patent is hereby corrected as shown below:

In column 4, line 18 after "described in" insert --co-pending--

Signed and Sealed this

Thirtieth Day of October, 2007

JON W. DUDAS
*Director of the United States Patent and Trademark Office*